(12) United States Patent
Judd et al.

(10) Patent No.: US 7,668,835 B2
(45) Date of Patent: Feb. 23, 2010

(54) MEDICAL IMAGE MANAGEMENT SYSTEM

(75) Inventors: Robert M. Judd, Chapel Hill, NC (US);
Enn-Ling Chen, Chapel Hill, NC (US);
Raymond J. Kim, Chapel Hill, NC (US)

(73) Assignee: Heart Imaging Technologies, LLC, Durham, NC (US)

( * ) Notice: Subject to any disclaimer, the term of this patent is extended or adjusted under 35 U.S.C. 154(b) by 471 days.

(21) Appl. No.: 11/069,221

(22) Filed: Feb. 28, 2005

(65) Prior Publication Data

US 2005/0251012 A1 Nov. 10, 2005

Related U.S. Application Data

(63) Continuation-in-part of application No. 09/742,575, filed on Dec. 20, 2000, now Pat. No. 6,934,698.

(51) Int. Cl.
G06F 17/30 (2006.01)
G06F 7/06 (2006.01)
G06F 7/14 (2006.01)

(52) U.S. Cl. .............. 707/10; 707/2; 707/9; 707/104.1
(58) Field of Classification Search .............. 707/104.1, 707/2, 9, 10; 600/407
See application file for complete search history.

(56) References Cited

U.S. PATENT DOCUMENTS

| | | | |
|---|---|---|---|
| 4,653,112 A | 3/1987 | Ouimette et al. |
| 5,321,520 A | 6/1994 | Inga et al. |
| 5,416,602 A | 5/1995 | Inga et al. |
| 5,467,471 A | 11/1995 | Bader |
| 5,546,580 A | 8/1996 | Seliger et al. |
| 5,715,823 A | 2/1998 | Wood et al. |
| 5,715,833 A | 2/1998 | Kleinhappl |
| 5,721,914 A | 2/1998 | SeVries |
| 5,724,578 A | 3/1998 | Morinaga et al. |
| 5,829,004 A | 10/1998 | Au |
| 5,832,488 A | 11/1998 | Eberhardt |
| 5,851,186 A | 12/1998 | Wood et al. |
| 5,891,035 A | 4/1999 | Wood et al. |
| 5,915,240 A | 6/1999 | Karpf |
| 5,995,943 A | 11/1999 | Bull et al. |
| 6,005,911 A | 12/1999 | Cheung |

(Continued)

FOREIGN PATENT DOCUMENTS

WO WO 98/24358 6/1998

OTHER PUBLICATIONS

Wong, S.T.C.; Tjandra, D.A., "A digital library for biomedical imaging on the Internet," Communications Magazine, IEEE, vol. 37, No. 1, pp. 84-91, Jan. 1999.*

(Continued)

Primary Examiner—Robert Stevens
(74) Attorney, Agent, or Firm—Neal Gerber & Eisenberg, LLP

(57) ABSTRACT

A method of managing medical information is disclosed. The method comprises the steps of receiving medical information in a format incompatible with the World Wide Web and converting the medical information to a format compatible with the World Wide Web. Further, the medical information is physically stored at a single location.

12 Claims, 24 Drawing Sheets

U.S. PATENT DOCUMENTS

| | | | |
|---|---|---|---|
| 6,018,713 | A | 1/2000 | Coli et al. |
| 6,032,120 | A | 2/2000 | Rock et al. |
| 6,047,081 | A | 4/2000 | Groezinger et al. |
| 6,076,066 | A | 6/2000 | DiRienzo et al. |
| 6,101,407 | A | 8/2000 | Groezinger |
| 6,159,150 | A | 12/2000 | Yale et al. |
| 6,171,244 | B1 | 1/2001 | Finger et al. |
| 6,178,225 | B1 | 1/2001 | Zur et al. |
| 6,210,327 | B1 | 4/2001 | Brackett et al. |
| 6,228,030 | B1 | 5/2001 | Urbano et al. |
| 6,236,881 | B1 | 5/2001 | Zahler et al. |
| 6,260,021 | B1 | 7/2001 | Wong et al. |
| 6,263,330 | B1 | 7/2001 | Bessette |
| 6,282,513 | B1 | 8/2001 | Stawder |
| 6,289,115 | B1 | 9/2001 | Takeo |
| 6,349,330 | B1 | 2/2002 | Bernadett et al. |
| 6,349,373 | B2 | 2/2002 | Sitka et al. |
| 6,381,029 | B1 | 4/2002 | Tipirneni |
| 6,415,295 | B1* | 7/2002 | Feinberg ................. 707/104.1 |
| 6,424,996 | B1 | 7/2002 | Killcommons et al. |
| 6,430,430 | B1 | 8/2002 | Gosche |
| 6,487,432 | B2 | 11/2002 | Slack |
| 6,487,599 | B1 | 11/2002 | Smith et al. |
| 6,556,698 | B1 | 4/2003 | Diano et al. |
| 6,574,629 | B1 | 6/2003 | Cooke, Jr. et al. |
| 6,603,494 | B1 | 8/2003 | Banks et al. |
| 6,635,016 | B2 | 10/2003 | Finkelshteins |
| 6,674,449 | B1 | 1/2004 | Banks et al. |
| 6,678,703 | B2 | 1/2004 | Rothschild et al. |
| 6,732,113 | B1* | 5/2004 | Ober et al. ................. 707/102 |
| 6,734,886 | B1* | 5/2004 | Hagan et al. ................ 715/853 |
| 6,775,670 | B2 | 8/2004 | Bessette |
| 6,829,378 | B2 | 12/2004 | DiFilippo et al. |
| 6,912,061 | B1 | 6/2005 | Ozaki |
| 6,934,698 | B2 | 8/2005 | Judd et al. |
| 6,959,339 | B1 | 10/2005 | Wu et al. |
| 7,039,723 | B2 | 5/2006 | Hu et al. |
| 7,158,979 | B2* | 1/2007 | Iverson et al. ............... 707/100 |
| 7,200,858 | B1 | 4/2007 | Benjamin et al. |
| 7,257,832 | B2 | 8/2007 | Beane et al. |
| 7,366,992 | B2 | 4/2008 | Thomas, III |
| 7,376,677 | B2* | 5/2008 | Ober et al. ................. 707/204 |
| 7,383,511 | B2 | 6/2008 | Tanaka et al. |
| 7,428,706 | B2* | 9/2008 | Hagan et al. ............... 715/738 |
| 7,457,656 | B2 | 11/2008 | Judd et al. |
| 7,519,591 | B2* | 4/2009 | Landi et al. .................... 707/6 |
| 7,526,485 | B2* | 4/2009 | Hagan et al. .................. 707/10 |
| 2001/0054155 | A1* | 12/2001 | Hagan et al. ................ 713/193 |
| 2002/0004727 | A1* | 1/2002 | Knaus et al. ................... 705/3 |
| 2002/0010679 | A1 | 1/2002 | Felsher |
| 2002/0016719 | A1* | 2/2002 | Nemeth et al. .................. 705/2 |
| 2002/0016923 | A1* | 2/2002 | Knaus et al. ................ 713/200 |
| 2002/0111833 | A1* | 8/2002 | Dick ............................. 705/3 |
| 2002/0116227 | A1* | 8/2002 | Dick ............................. 705/3 |
| 2002/0177757 | A1* | 11/2002 | Britton ....................... 600/300 |
| 2003/0039362 | A1* | 2/2003 | Califano et al. ............. 380/283 |
| 2004/0015372 | A1 | 1/2004 | Bergman et al. |
| 2004/0088355 | A1* | 5/2004 | Hagan et al. ................ 709/203 |
| 2004/0117215 | A1* | 6/2004 | Marchosky .................... 705/3 |
| 2004/0143594 | A1* | 7/2004 | Kalies .................... 707/103 R |
| 2004/0193901 | A1 | 9/2004 | Bharara |
| 2004/0267703 | A1* | 12/2004 | McEnery et al. ................ 707/3 |
| 2005/0114334 | A1* | 5/2005 | Ober et al. ...................... 707/9 |
| 2005/0177050 | A1* | 8/2005 | Cohen ........................ 600/509 |
| 2005/0187794 | A1* | 8/2005 | Kimak ........................... 705/3 |
| 2005/0256839 | A1 | 11/2005 | Leong et al. |
| 2006/0004772 | A1* | 1/2006 | Hagan et al. .................. 707/10 |
| 2006/0064321 | A1 | 3/2006 | Sasano et al. |
| 2006/0155578 | A1* | 7/2006 | Eisenberger et al. ........... 705/2 |

OTHER PUBLICATIONS

Wong, Stephen T. C., et al., "A Digital Library for Biomedical Imaging on the Internet", IEEE Communications Magazine, vol. 37, Issue 1, Jan. 1999, pp. 84-91.*

Rohm, Andrew J., et al., "Just What the Doctor Ordered: the Role of information Sensitivity and Trust in Reducing Medical Information Privacy Concern", Journal of Business Research, vol. 57, Issue 9, Sep. 2004, pp. 1000-1011.*

Lui, Chien-Tsai, et al., "Sharing Patient Care Records Over the World Wide Web", International Journal of Medical Informatics, vol. 61, Issues 2-3, May 2001, pp. 189-205.*

Berman, Jules J., "Concept-Match Medical Data Scrubbing: How Pathology Text Can Be Used in Research", Arch Pathol Lab Med, vol. 127, Jun. 2003, pp. 680-686.*

Douglass, M., et al., "Computer-Assisted De-Identification of Free Text in the MIMIC II Database", Computers in Cardiology, Sep. 19-22, 2004, pp. 341-344.*

Cody, Patrick M., "Dynamic Security for Medical Record Sharing", Massachusetts Institute of Technology, Master of Engineering in EE and CS Thesis, Aug. 28, 2003, pp. 1-53.*

Office Action dated Oct. 20, 2009 for U.S. Appl. No. 11/067,021.*

Wong, S., "Interactive Query and Visualization of Medical Images on the World Wide Web," Proceedings of the SPIE, 1995, pp. 390-401.

Ratib, O., "Self-contained off-line medial for exchanging medical images using DICOM-complaint standard," Proceedings of the SPIE, 2000, pp. 30-34.

Wong, S., "A Hospital Integrated Framework for Multimodality Image Base Management," IEEE Transactions on Systems, Man, and Cybernetics, 1996, pp. 455-469.

Kitney, R.I., et al.; "An Object Oriented Multi-Modality Display and Analysis System Incorporating DICOM3;" Computers in Cardiology; 1994; pp. 181-183.

Office Action dated Apr. 30, 2009 for U.S. Appl. No. 11/238,409.

Notice of Allowance dated Oct. 6, 2008 for U.S. Appl. No. 10/999,544.

Office Action dated Oct. 31, 2008 for U.S. Appl. No. 11/238,409.

Office Action dated Jan. 7, 2009 for U.S. Appl. No. 11/063,389.

Final Office Action dated Mar. 3, 2009 for U.S. Appl. No. 11/067,021.

Mezrich, R.S., et al., "Radiology on the Information Superhighway", Radiology 1995; 195:73-81.

"Personalized Web Presentation of Computer-based Patient Records", Proceedings of Healthcare Information and Management Systems Society conference (HIMSS '98), Orlando, Florida, vol. 4, 1998, pp. 11-24.

Office Action dated Jun. 26, 2008 for U.S. Appl. No. 11/067,021.

Office Action dated Jul. 23, 2008 for U.S. Appl. No. 11/067,022.

* cited by examiner

—OR—

STEP 4020 – DEFINE SEARCH REGION AS SUBREGION WITHIN IMAGE WHICH CONTAINS THE ORGAN OF INTEREST (EG. HEART) AND SEARCH ALL MOVIE FRAMES FOR THE SINGLE BRIGHTEST PIXEL. SCALE ALL MOVIE FRAMES BY SAME AMOUNT TO MAKE SINGLE BRIGHTEST PIXEL EQUAL TO 2 TO THE 8TH POWER MINUS 1, EG. 255 (1 BYTE/PIXEL, 8-BIT IMAGE).

STEP 4030 – CREATE THUMBNAIL MOVIES BY CROPPING IMAGES SUCH THAT ONLY THE ORGAN OF INTEREST IS SHOWN (EG. HEART).

STEP 4040 – CONVERT ALL MOVIE FRAMES INTO A SINGLE MOVIE WITH FRAME RATE CHOSEN TO SIMULATE REAL TIME MOTION (EG. BEATING HEART)

STEP 4050 – CREATE A FULL-FIELD-OF-VIEW VERSION OF EACH THUMBNAIL SO THAT USER CAN DOUBLE-CLICK TO VIEW ADDITIONAL DETAILS.

FIG. 7A

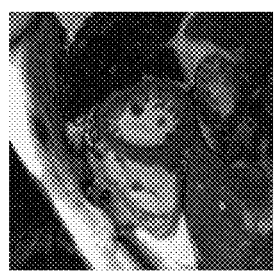
FIG. 7C
EG. STEP 4040
THUMBNAIL MOVIE OF BEATING HEART
(16 FRAMES=100KB)
EG. STEP 4050
FULL FIELD-OF-VIEW MOVIE DISPLAYED FULL SCREEN WHEN THUMBNAIL CLICKED
(16 FRAMES=400KB)

DATABASE TABLE STORED AT
"imagedatabase.com"

| Name | Provider | MRN | Type | URL |
|---|---|---|---|---|
| | (other data) | (other data) | (...) | (other data) |
| | Hospital A | Patient_123 | MRI | http://www.hospital_a/mr_789 |
| | Hospital A | Patient_123 | US | http://www.hospital_a/us_789 |
| | Drug Store A | Patient_456 | drug | http://www.drug_store_a/drug_012 |
| | (other data) | (other data) | (...) | (other data) |

AFTER STEP 1806

| Name | Provider | MRN | Type | URL |
|---|---|---|---|---|
| | (other data) | (other data) | (...) | (other data) |
| Jones | Hospital A | Patient_123 | MRI | http://www.hospital_a/mr_789 |
| Jones | Hospital A | Patient_123 | US | http://www.hospital_a/us_789 |
| Jones | Drug Store A | Patient_456 | drug | http://www.drug_store_a/drug_012 |
| | (other data) | (other data) | (...) | (other data) |

AFTER STEP 1807

Clinical (Private) Database View

Research (Public) Database View

FIGURE 19

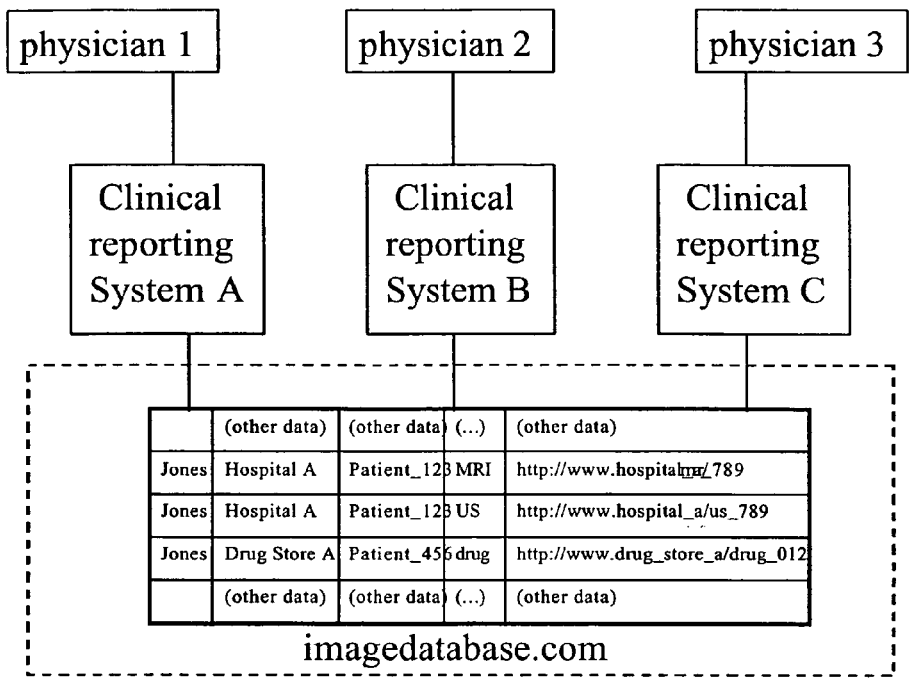
STEP 1806 - METHOD A
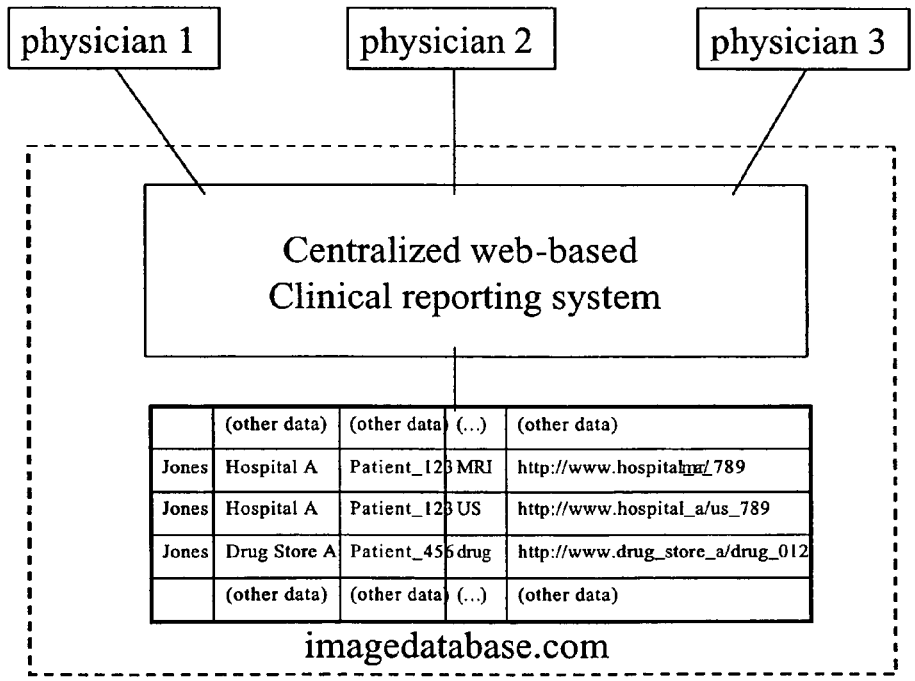
STEP 1806 - METHOD B
FIGURE 22

MEDICAL IMAGE MANAGEMENT SYSTEM

Cross-Reference to Related Application

This application is a continuation-in-part application of U.S. application Ser. No. 09/742,575 filed on Dec. 20, 2000, which issued as U.S. Pat. No. 6,934,698 on Aug. 23, 2005 entitled "Medical Image Management System."

FIELD OF THE PRESENT INVENTION

The Present Invention relates to medical imaging. Specific exemplary embodiments discussed relate to cardiac medical imaging.

BACKGROUND OF THE PRESENT INVENTION

The description of the references in this Section is not intended to constitute an admission that any reference referred to herein is "Prior Art" with respect to the Present Invention, unless specifically designated as such.

Medical imaging is important and widespread in the diagnosis of disease. In certain situations, however, the particular manner in which the images are made available to physicians and their patients introduces obstacles to timely and accurate diagnoses of disease. These obstacles generally relate to the fact that each manufacturer of a medical imaging system uses different and proprietary formats to store the images in digital form. This means, for example, that images from a scanner manufactured by General Electric Corp. are stored in a different digital format compared to images from a scanner manufactured by Siemens Medical Systems. Further, images from different imaging modalities, such as, for example, ultrasound and magnetic resonance imaging (MRI), are stored in formats different from each other. Although it is typically possible to "export" the images from a proprietary workstation to an industry-standard format such as "Digital Imaging Communications in Medicine" (DICOM), Version 3.0, several limitations remain as discussed subsequently. In practice, viewing of medical images typically requires a different proprietary "workstation" for each manufacturer and for each modality.

Currently, when a patient describes symptoms, the patient's primary physician often orders an imaging-based test to diagnose or assess disease. Typically, days after the imaging procedure, the patient's primary physician receives a written report generated by a specialist physician who has interpreted the images. The specialist physician, however, typically has not performed a clinical history and physical examination of the patient and often is not aware of the patient's other test results. Conversely, the patient's primary physician typically does not view the images directly but rather makes a treatment decision based entirely on written reports generated by one or more specialist physicians. Although this approach does allow for expert interpretation of the images by the specialist physician, several limitations are introduced for the primary physician and for the patient, such as, for example:

(1) The primary physician does not see the images unless he travels to another department and makes a request;
(2) It is often difficult to find the images for viewing because there typically is no formal procedure to accommodate requests to show the images to the primary physician;
(3) Until the written report is forwarded to the primary physician's office, it is often difficult to determine if the images have been interpreted and the report generated;
(4) Each proprietary workstation requires training in how to use the software to view the images;
(5) It is often difficult for the primary physician to find a technician who has been trained to view the images on the proprietary workstation;
(6) The workstation software is often "upgraded" requiring additional training;
(7) The primary physician has to walk to different departments to view images from the same patient but different modalities;
(8) Images from the same patient but different modalities cannot be viewed side-by-side, even using proprietary workstations;
(9) The primary physician cannot show the patient his images in the physician's office while explaining the diagnosis; and
(10) The patient cannot transport his images to another physician's office for a second opinion.

It would be desirable to allow digital medical images to be viewed by multiple individuals at multiple geographic locations without loss of diagnostic information.

A similar barrier to accessing medical information exists for researchers interested in studying the effects of medical treatments on populations of patients. Because the medical information is stored in dissimilar digital formats on dissimilar medical information systems, a significant percentage of the overall cost of a research study can be attributed to the effort of extracting and converting the digital records into the format desired by the individual researcher. For research, unlike for clinical care, an additional barrier is introduced by the legal requirements which protect patients' privacy. Widely-recognized strategies to protecting patient privacy are: 1) Seeking each patient's written permission to be studied; and 2) De-Identifying the medical information in such a way that the patient's identity cannot be determined, i.e., by removing the patient's name from the medical information. De-Identification of medical records, while useful, often results in a loss of the information needed to associate multiple records from the same patient with each other (e.g., the patient's name). It would be desirable to allow multiple digital medical records associated with a single patient to be accessed by multiple researchers at multiple geographic locations without violating the patients' right to privacy.

"Teleradiology" allows images from multiple scanners located at distant sites to be transferred to a central location for interpretation and generation of a written report. This model allows expert interpreters at a single location to examine images from multiple distant geographic locations. Teleradiology does not, however, allow for the examination of the images from any site other than the central location, precluding examination of the images by the primary physician and the patient. Rather, the primary physician and the patient see only the written report generated by the interpreters who examined the images at the central location. In addition, this approach is based on specialized "workstations" (which require substantial training to operate) to send the images to the central location and to view the images at the central location. It would be advantageous to allow the primary physician and the patient to view the images at other locations, such as the primary physician's office, at the same time he/she and the patient see the written report and without specialized hardware or software.

In principle, medical images could be converted to Internet Web Pages for widespread viewing. Several technical limitations of current Internet standards, however, create a situation where straightforward processing of the image data results in images which transfer across the Internet too slowly, lose diagnostic information or both. One such limitation is the bandwidth of current Internet connections which, because of the large size of medical images, result in transfer times which are unacceptably long. The problem of bandwidth can be addressed by compressing the image data before transfer, but compression typically involves loss of diagnostic information. In addition, due to the size of the images the time required to process image data from an original format to a format which can be viewed by Internet browsers is considerable, meaning that systems designed to create Web Pages "on the fly" introduce a delay of seconds to minutes while the person requesting to view the images waits for the data to be processed. Workstations allow images to be reordered or placed "side-by-side" for viewing, but again, an Internet system would have to create new Web Pages "on the fly" which would introduce further delays. Finally, diagnostic interpretation of medical images requires the images are presented with appropriate brightness and contrast. On proprietary workstations these parameters can be adjusted by the person viewing the images but control of image brightness and contrast are not features of current Internet standards (such as, for example, http or html).

It is possible to allow browsers to adjust image brightness and contrast, as well as other parameters, using "Java" programming. "Java" is a computer language developed by Sun Microsystems specifically to allow programs to be downloaded from a server to a client's browser to perform certain tasks. Using the "Java" model, the client is no longer simply using the browser to view "static" files downloaded from the server, but rather in addition the client's computer is running a program that was sent from the server. There are several disadvantages to using "Java" to manipulate the image data. First, the user must wait additional time while the "Java" code is downloaded. For medical images, the "Java" code is extensive and download times are long. Second, the user must train to become familiar with the controls defined by the "Java" programmer. Third, the user must wait while the "Java" code processes the image data, which is slow because the image files are large. Fourth, "Java" code is relatively new and often causes browsers to "crash." Finally, due to the "crashing" problem "Java" programmers typically only test their code on certain browsers and computers, such as Microsoft Explorer on a PC, precluding widespread use by owners of other browsers and other computer platforms.

Wood et al., U.S. Pat. No. 5,891,035 ("Wood"), the contents of which are hereby incorporated by reference in their entirety, describe an ultrasound system which incorporates an http server for viewing ultrasound images over the Internet. The approach of Wood, however, creates Web Pages "on the fly," meaning that the user must wait for the image processing to complete. In addition, even after processing of the image data into a Web Page the approach of Wood does not provide for processing the images in such as way that excessive image transfer times due to limited bandwidth are addressed or provide for "brightness/contrast" to be addressed without loss of diagnostic information. In addition, the approach of Wood is limited to ultrasound images generated by scanners manufactured by a single company, and does not enable viewing of images from modalities other than ultrasound.

FIG. 1 summarizes a common prior art approach currently used by companies to serve medical images to Internet browsers (e.g., General Electric's "Web-Link" component of their workstation-based "Picture Archiving and Communication System" (PACS)). As can be seen in FIG. 1, serial processing of image data "on the fly" combined with extensive user interaction results in a slow, expensive, and unstable system.

Referring to FIG. 1, after a scanner acquires images (Step 100) a user may request single image as a webpage (Step 200) whereby the image data is downloaded (Step 300) to allow the user to view a single image with the single image (Step 400). Steps 1000-1400 result in extensive user interaction which results in the system being slow, expensive and unstable.

While the Present Invention relates to medical imaging generally, it will be better understood within the discussion of exemplary embodiments directed toward cardiac imaging.

SUMMARY OF THE PRESENT INVENTION

The Present Invention proceeds from the realization that if medical images of different formats could be processed in such a way that limitations of current Internet standards could be overcome, any standard Internet browser could be used as a diagnostic workstation to allow any medical image to be viewed from any location on earth without specialized hardware or software. Once this goal has been achieved, the following actions becomes possible:

(1) To notify the primary physician via e-mail or pager as soon as the imaging has been completed;
(2) For the primary physician to view the images with a single "double click";
(3) To view the images at the same time the primary physician and/or the patient reads the written report;
(4) To view images of the same patient but from different modalities side-by-side;
(5) To view images of the same patient and same modality but different time points side-by-side to assess the progression of disease;
(6) For the primary physician to discuss the images over the telephone with another physician who is viewing the same images simultaneously at another location;
(7) To make diagnoses and clinical treatment plans from anywhere in the World, including the physician's home;
(8) To discuss the images with the patient in the physician's office or over the telephone with the patient at home;
(9) For the patient to present the images to another physician for a second opinion; and
(10) For the patient to move to a different city/state/country and have the images "move" with him/her.

Furthermore, once the standard Internet browser can be used as a diagnostic workstation, it becomes feasible to construct a Worldwide database of medical images using a predefined hierarchical Internet addressing structure. This structure would allow for the unique address of all medical images for all persons throughout their lifetime.

Accordingly, one embodiment of the Present Invention is directed toward a method of managing medical images. A plurality of medical images created by a plurality of medical imaging devices, each of which processes the medical image using a unique image format, is received. The medical images are then converted to a common image format suitable for display on a computer screen. Preferably the method comprises posting the converted images for access via a client computer. Browser compatible pages having embedded tags corresponding to the converted images are preferably generated and posted with the converted images.

Another embodiment of the Present Invention is directed towards a medical image database comprising images corresponding to a plurality of different modalities. The database is preferably organized in a hierarchical data structure where the data structure comprises a patient identifier parameter and an image modality identifier parameter. The image identifier parameter is associated with at least one of the plurality of modalities. The patient identifier parameter is preferably at a higher level in the hierarchical data structure than the image modality identifier parameter.

In one method of managing medical images according to the Present Invention, images are pulled from a scanner in response to a user request. The pulled images are converted to a common image format compatible for display at a computer. The converted images are then posted for display at a client computer. Preferably, the method includes displaying to a user at the client computer a selection comprising images associated with at least two different modalities. The method also preferably comprises simultaneously displaying on a screen a medical image to a first user at a first location and a second user at a second location.

A medical image system, according to the Present Invention, comprises a medical image management system. In a preferred embodiment, the medical image management system comprises a transfer engine for receiving image data from a scanner; a converter engine connected to receive images from the transfer engine and convert the images to a browser compatible format; and a post engine connected to receive images from the converter engine and post the images for subsequent access by a user.

In a preferred embodiment, the converter engine comprises a decoding engine for extracting raw image data; and a physiologic knowledge engine adapted to receive data from the decoding engine. The physiologic knowledge engine adjusts the image quality and reduces the size of the image data, which is then transferred to a post engine. The physiologic knowledge engine is primarily responsible for reducing the image file size without loss of diagnostic data though other aspects of the Present Invention are used to reduce file size while maintaining viability of the data. The encoding engine converts the image data to browser compatible image data.

Other objects and advantages of the Present Invention will be apparent to those of skill in the art from the teachings herein.

BRIEF DESCRIPTION OF THE DRAWINGS

In the interest of enabling one of skill in the art to practice the Present Invention, exemplary embodiments are shown and described. For clarity, details apparent to those of skill in the art and reproducible without undue experimentation are generally omitted from the drawings and description.

FIG. 7A describes a method for reducing image data file size without loss of diagnostic information;

FIG. 7C depicts the diagnostic search area in both representative thumbnail size and full screen size with corresponding file sizes indicated;

FIG. 19 depicts the effects of steps 1806 and 1807 on the database table hosted by "imagedatabase.com;"

FIG. 22 depicts two possible methods by which step 1806 populates the database table hosted at "imagedatabase.com".

Figure 1:
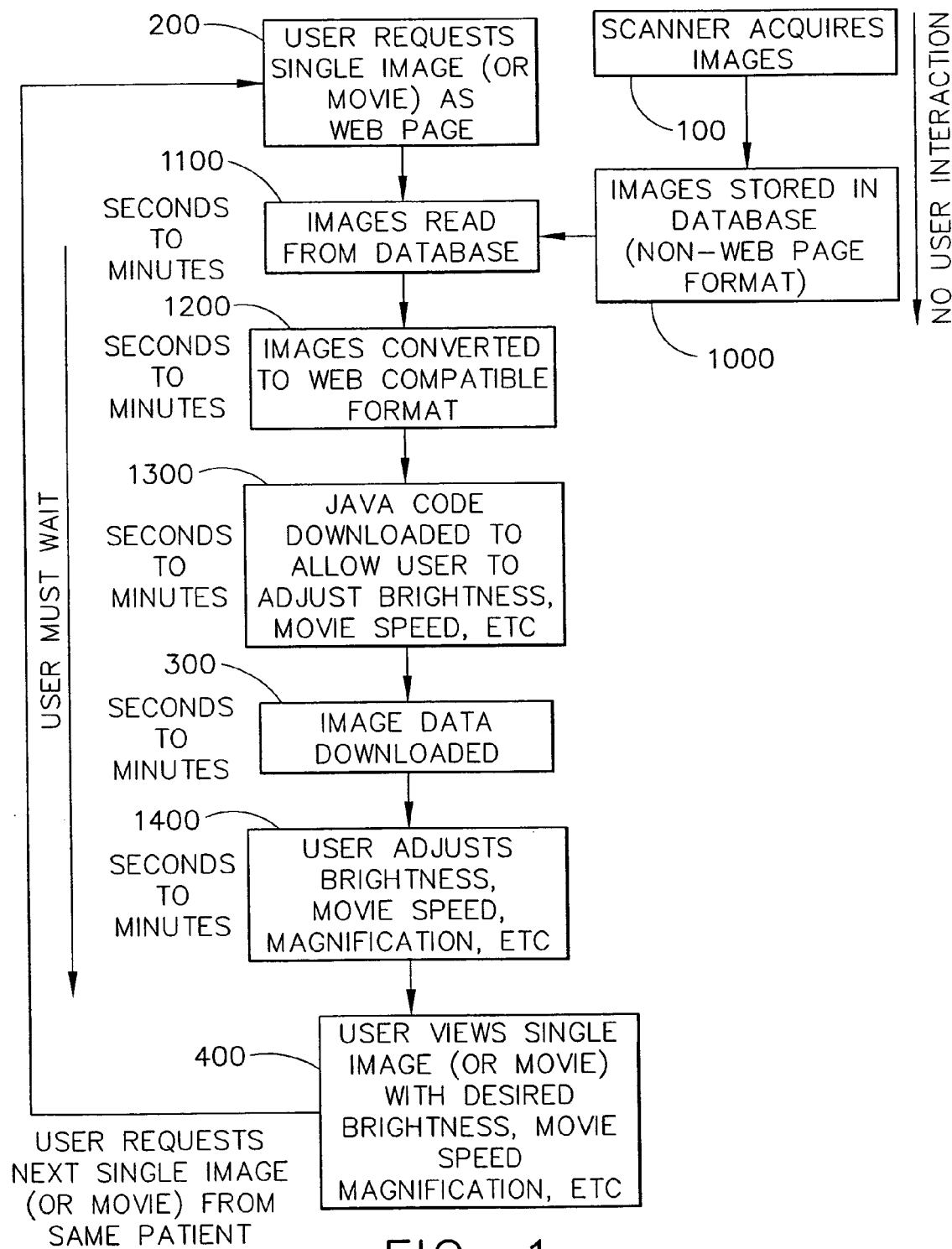
FIG. 1 depicts a prior art method for user to view images from a scanner.

DESCRIPTION OF EXEMPLARY
EMBODIMENTS OF THE PRESENT
INVENTION

The Present Invention is discussed in relation to imaging with specific applications discussed in relation to cardiac images; however, other uses will be apparent from the teachings disclosed herein. The Present Invention will be better understood from the following detailed description of exemplary embodiments, with reference to the attached figures, wherein like reference numerals and characters refer to like parts, and by reference to the following Claims.

It will be apparent to one possessing ordinary skill in the art that the structure, methods and systems described herein regarding a medical image management system are additionally and inherently applicable to the management of multiple types of medical information, such as, for example, medical imaging reports, electrocardiograms, medical test results, patient demographics, clinic reports, procedure reports, in-patient summary reports and the like.

The herein-described Present Invention has been constructed and tested on images of the heart acquired using a variety of modalities. The images have been pulled from commercial scanners, processed without loss of diagnostic information, adjusted with respect to brightness and contrast, and posted on Internet Web Pages for viewing.

Figure 2:
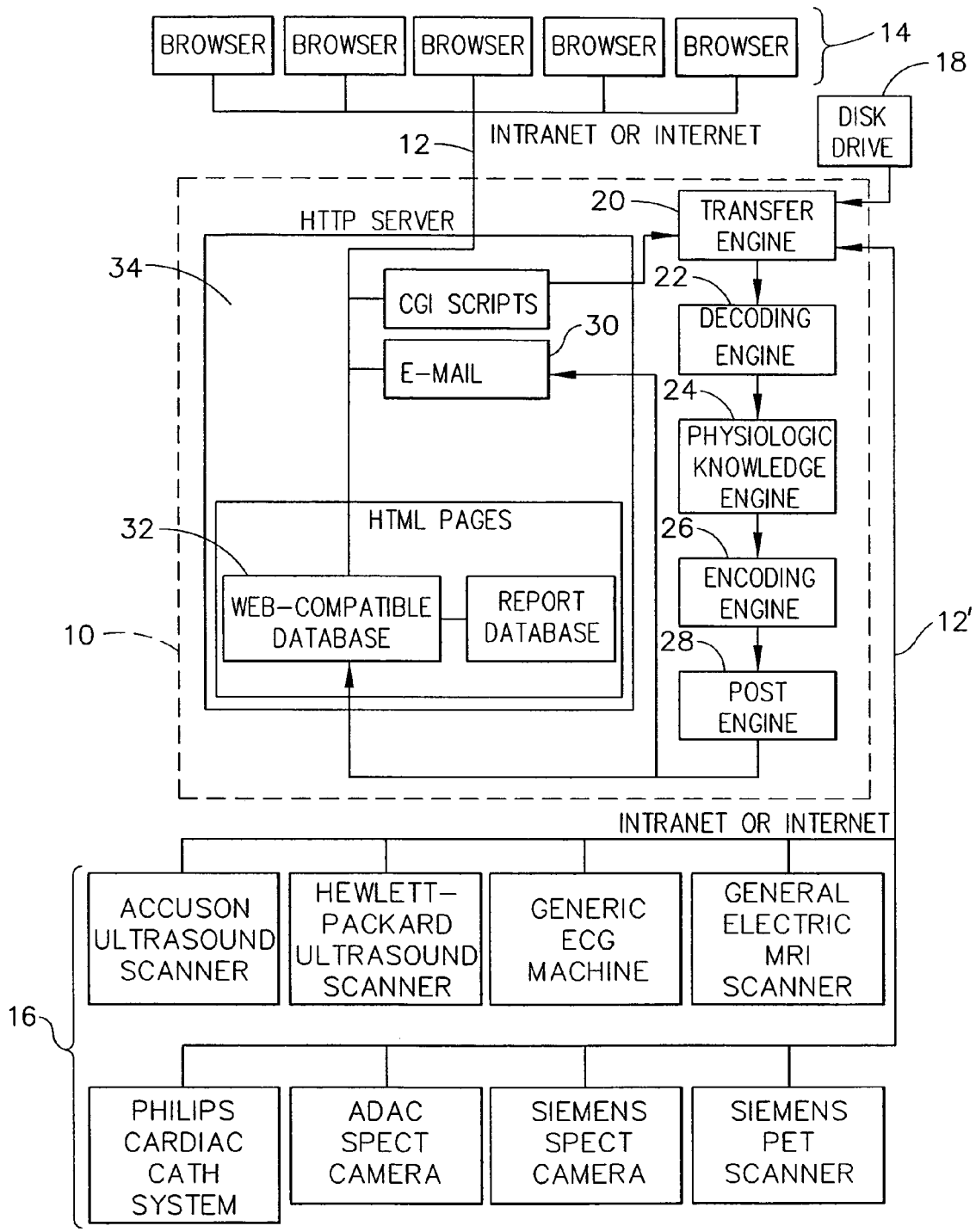
FIG. 2 depicts a block diagram of an imaging managing system according to an embodiment of the Present Invention.
Figure 3:
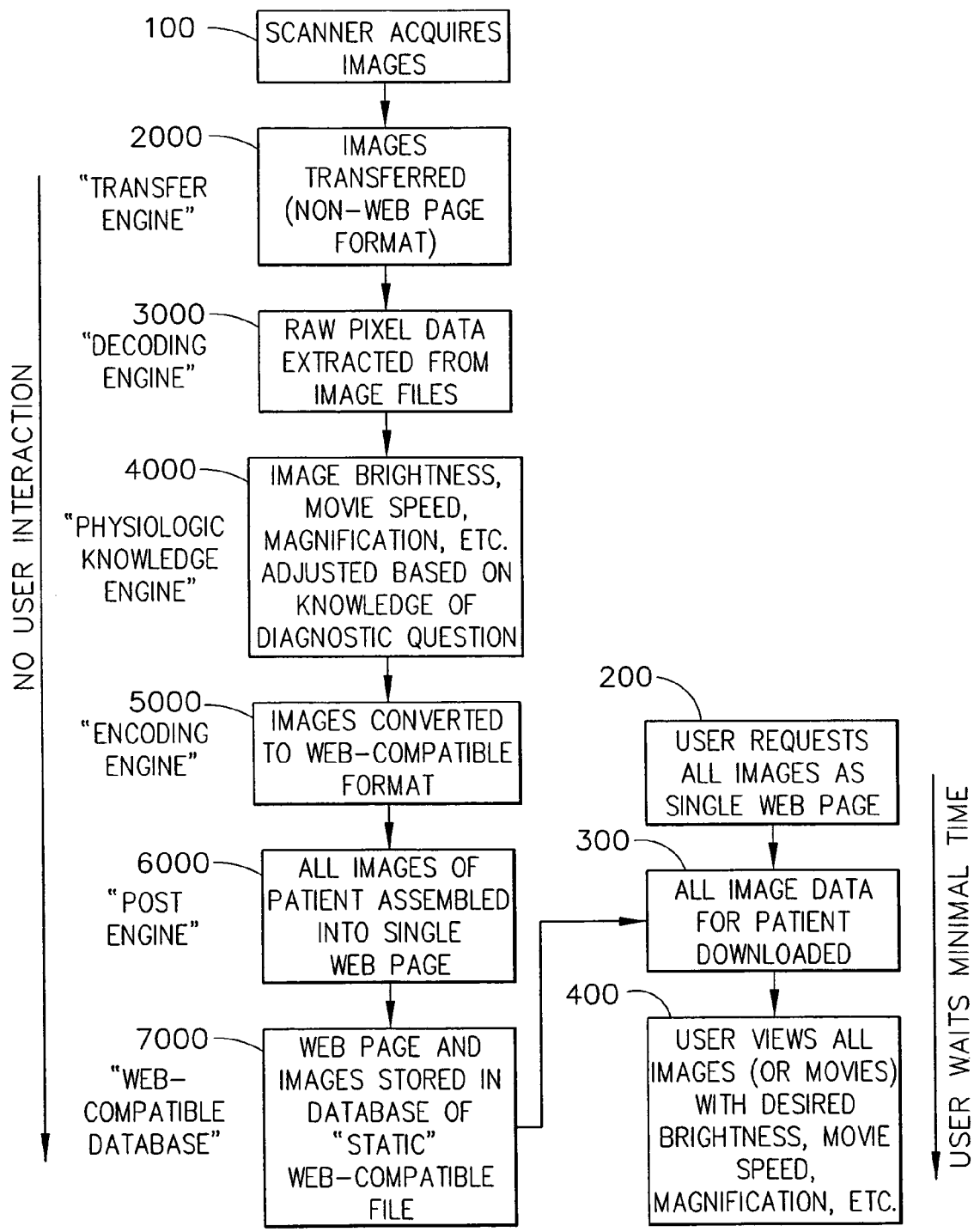
FIG. 3 depicts a system overview of an embodiment of the Present Invention for providing a user with images from a scanner.

FIGS. 2 and 3 show the process in schematic form. In FIG. 2, a medical image management system 10 is connected via a Hospital Intranet or the Internet 12 to a number of browsers 14 (such as, for example, Microsoft Explorer™ or Netscape Navigator™). The connection 12 to the browsers is used to: 1) Accept commands to pull images from the scanners 16; 2) To navigate through images which have already been posted as web pages; and 3) To arrange and organize images for viewing. The medical image management system 10 is also connected to a number of medical imaging systems (scanners) 16 via a Hospital Intranet or the Internet 12'. The connection 12' to the scanners 16 is used to pull the images by Internet-standard file transfer protocols (FTP). Alternatively, images can be transferred to the system 10 via a disk drive or disk 18 (see FIGS. 2 and 3).

Preferably the scanner, and hence modality, is associated with magnetic resonance imaging, echocardiographic imaging, nuclear scintigraphic-imaging (e.g., SPECT, or single photon emission computed tomography), positron emission tomography, x-ray imaging and combinations thereof.

Responsibility for the entire process is divided amongst a series of software engines. The processes of the transfer engine 20, decoding engine 22, physiologic knowledge engine 24, encoding engine 26 and post engine 28 (FIGS. 2 and 3) are preferably run automatically by computer and do not require the person using the browser, the user, to wait for completion of the associated tasks. The decoding engine 22, physiologic knowledge engine 24 and encoding engine 26 are, preferably, combined to form a converter engine. The post engine 28 sends an e-mail notification, via an e-mail server 30 (FIG. 2) to the person submitting the request when the computations are complete, thereby allowing the requester to do other tasks. Similarly, text messages could be sent to a physician's pager. The time necessary for these computations depends on the size of the images and the speed of the network, but was measured for the MRI images of FIG. 16 to be approximately 3 minutes over a standard Ethernet 10BASET line (10 Mbps) using a 400 MHz computer.

Figure 4A:
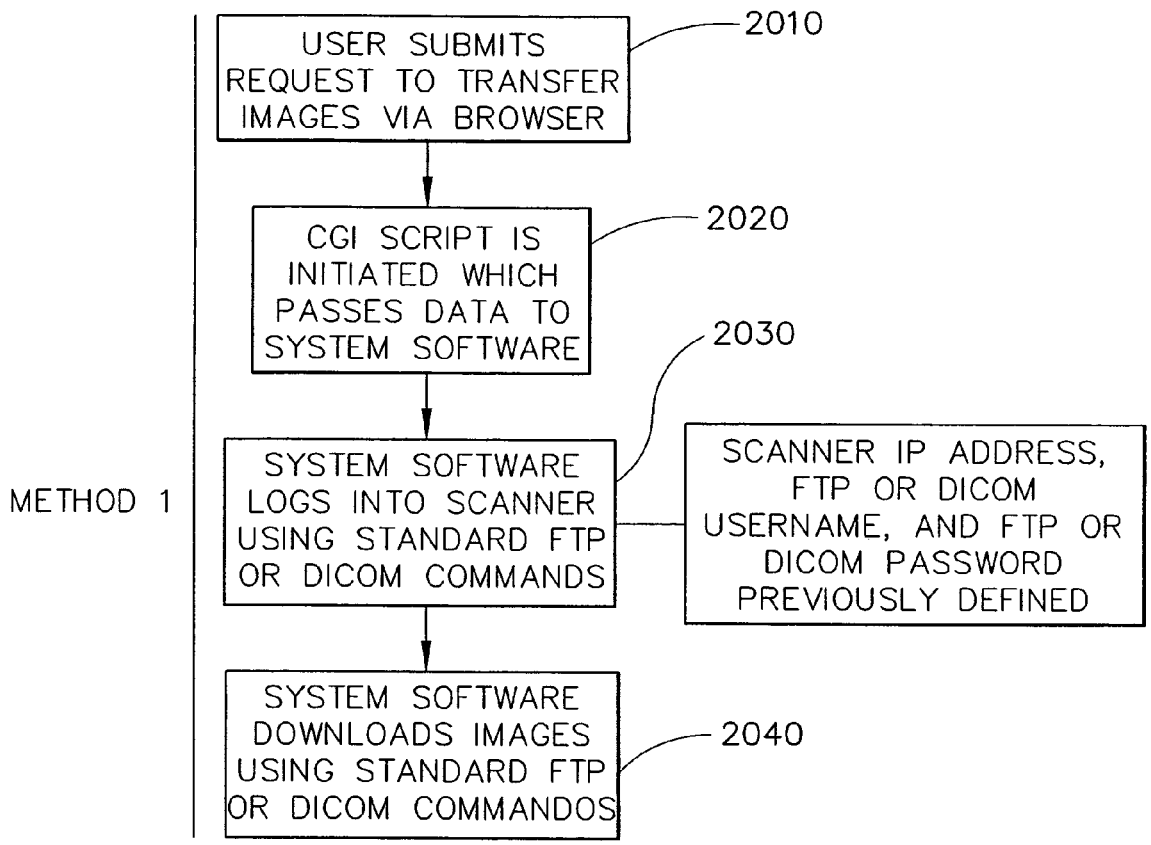
FIG. 4A depicts steps for affecting transfer of images from a scanner.
Figure 4B:
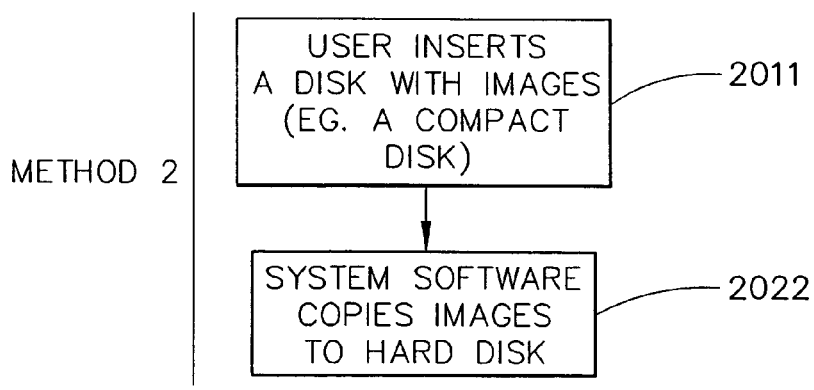
FIG. 4B depicts an alternate method for obtaining images from a scanner via a disk having the images stored thereon.

The transfer engine 20 is responsible for pulling the images from the scanner 16 for example, in response to a user request (Step 2010). (FIGS. 2 and 3, details in FIG. 4). Using previously recorded information such as, for example, a username and password (Step 2020), the transfer engine 20 logs into the scanner 16 over the Internet 12 (Step 2030) and pulls the appropriate images from the scanner 16, using standard Internet FTP or DICOM commands (Step 2040). Alternatively, images can be acquired by the transfer engine 20 by use of a disk drive 18 such as, for example, a CD-ROM drive (FIGS. 2-4) (Steps 2011-2022). When the transfer process is complete, all images from the scan will exist within the transfer engine 20 but are still in their original digital format. This format may be specific to the scanner 16 manufacturer, or may be one of a variety of formats which are standard but cannot be displayed by browsers, such as, for example, DICOM. The images are then passed to the decoding engine (Step 3000).

Figure 5A:
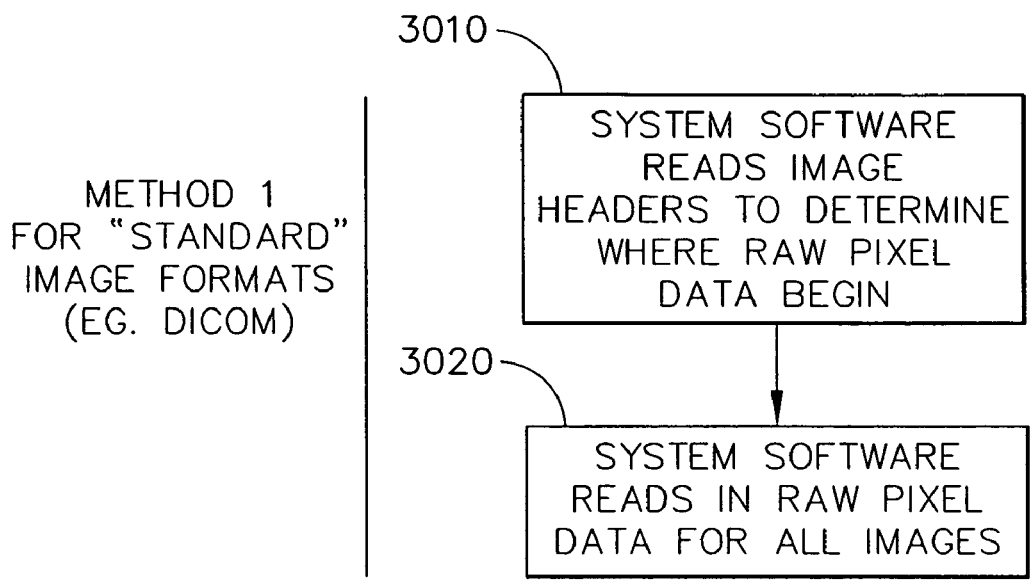
FIG. 5A depicts a method for extracting raw pixel data from a standard image data format.
Figure 5B:
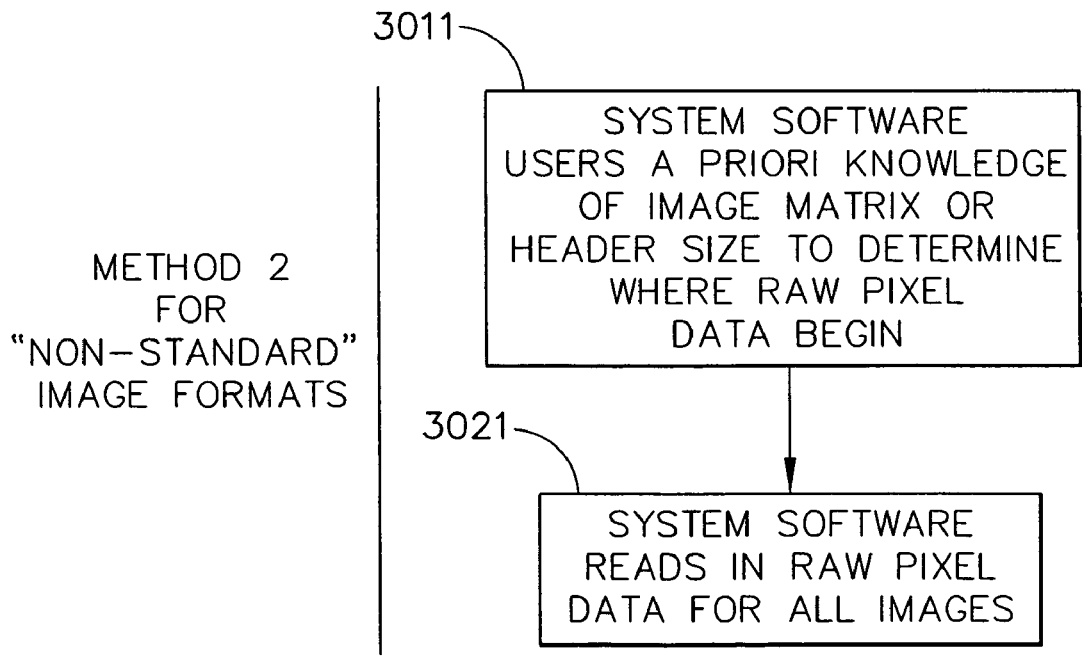
FIG. 5B depicts a method for extracting raw pixel data from a non-standard image format.

The decoding engine 22 (FIG. 5) is responsible for extracting the raw image pixel data from the original, differing, non-Web compatible digital formats that the transfer engine 20 acquired. In the case of standard formats, such as, for example, DICOM, this can be accomplished by reading published file structures and writing computer code to read this format (Steps 3010-3020). In the case of non-standard formats, successful extraction of the image data proceeds from the realization that all formats differ from each other mainly in the header region of the image file, i.e., the part which contains information like the patient name, scan date, name of hospital, etc. (Steps 3011-3021.) Because the most important information such as patient name and scan date can be input via the web-based form pages upon submission (see FIGS. 14-17, for example), extraction of the image data for non-standard formats can be accomplished by ignoring the header data entirely and reading only the image data. Typically, the image data are stored as a series of pixel values starting at the upper left corner of the image and proceeding across each row of pixels from left to right and then repeating this process for all rows of the image (i.e., top to bottom).

Figure 6:
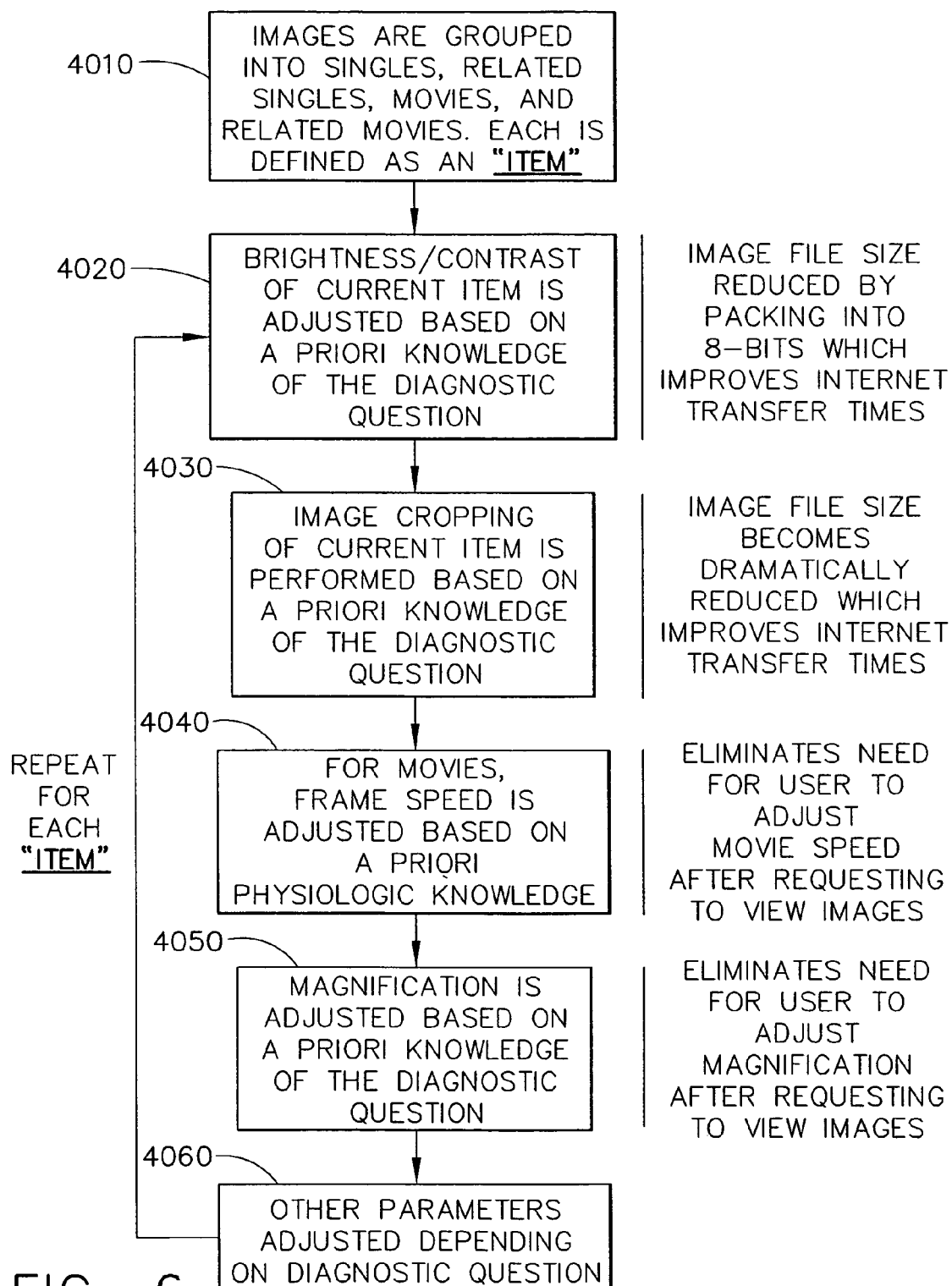
FIG. 6 depicts a method for reducing image data files without loss of diagnostic data.
Figure 7B:
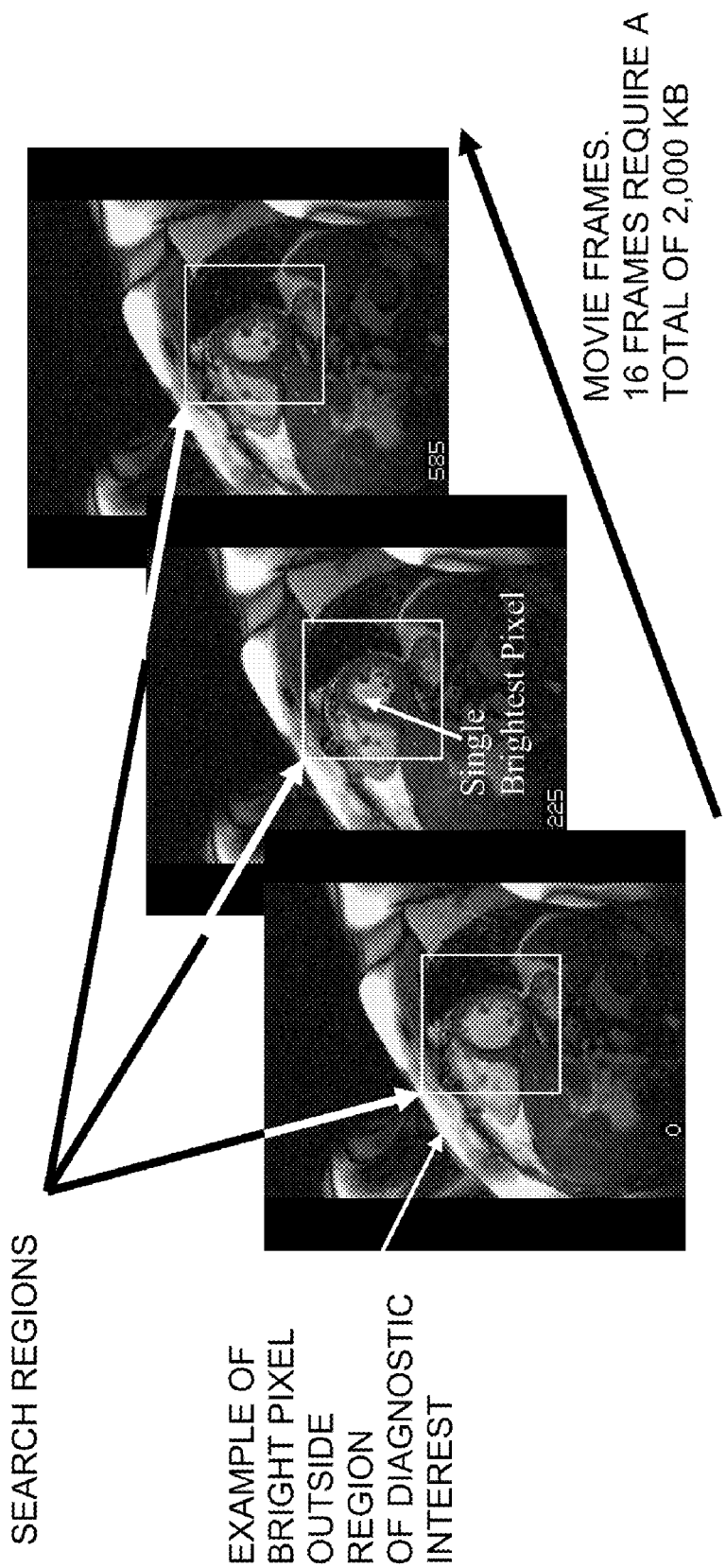
FIG. 7B pictorially depicts selecting a bright pixel in a diagnostic search region.

The physiologic knowledge engine 24 (FIG. 6) is responsible for adjusting image brightness and contrast, adjusting image magnification, adjusting movie frame speed and other image parameters important for diagnosis (Step 4010-4020). The physiologic knowledge engine 24 is also responsible for reducing the size of the images to allow acceptable transfer times at current Internet bandwidths without loss of diagnostic information (Step 4030). These tasks are achieved in part by the use of a priori knowledge of physiology, anatomy, the diagnostic question or any combination of the three. One aspect of this is the realization that the human eye is capable of distinguishing less than 256 distinct levels of gray in a medical image, and that most of the field-of-view (FOV) of the image is not of diagnostic interest. The grayscale limitations of the human eye imply that any medical image can be compressed to 8-bits of grayscale levels and that, if appropriately scaled, the resulting image will have appropriate brightness/contrast without the need to adjust these using the Web browser (FIG. 7A, Step 4020). This is important because adjustment of brightness/contrast by the browser is not part of existing Internet standards. Another important piece of a priori information is that much of the FOV is not of diagnostic interest (Step 4030 and FIG. 7B). This implies that the images can be cropped which allows a significant reduction in the size of the image file. This is important because limitations of existing Internet bandwidths result in excessive image transfer times if the file size is not reduced.

An example of how the physiologic knowledge engine 24 functions is given in FIGS. 7A-7C for the specific case of MRI of the heart. In Step 4020, the region of the image which contains the organ of diagnostic interest is defined (e.g. the heart). For the general case of a group of images which are intended to be played as a movie to depict time-varying quantities (e.g. heart motion), the physiologic knowledge engine 24 searches all movie frames for the single brightest pixel within the search region (e.g. within the heart). All pixels of all movie frames are then scaled such that the single brightest pixel within the search region of all frames equal 255 (e.g., 8-bit image). After this Step, the image brightness/contrast are appropriate for the organ of interest without loss of diagnostic information.

In Step 4030, thumbnail movies are extracted for which the FOV is reduced by cropping the images to contain only the organ of interest (e.g., the heart). For a typical file size of 2,000 KB for a movie with 16 frames, the processes herein described would result in a 20-fold reduction in movie file size for the thumbnails (to 100 KB) and 6-fold for full FOV images (to 400 KB) (See FIG. 7C). These file sizes imply that every still-frame and every movie from an entire patient scan can be transferred over the Internet as thumbnails in a few seconds.

In Step 4040, the frame rate is chosen to simulate real-time motion (e.g., a beating heart would have all frames play within one heart beat or about 1 second). In Step 4050, full FOV images are created with a magnification which fills the user's entire screen because this is what a cardiologist would like to see for a heart image. Each thumbnail can be "clicked" by the mouse to initiate transfer of the entire FOV for that movie, also in a few seconds. Importantly, this is achieved without loss of diagnostic information, without the need to adjust brightness/contrast, and without the need to adjust the frame rate of the movie. Step 4060 comprises adjusting other parameters, if warranted. When the physiologic knowledge engine 24 has completed these tasks on all images from a given patient, they are passed to the encoding engine 26.

Figure 8:
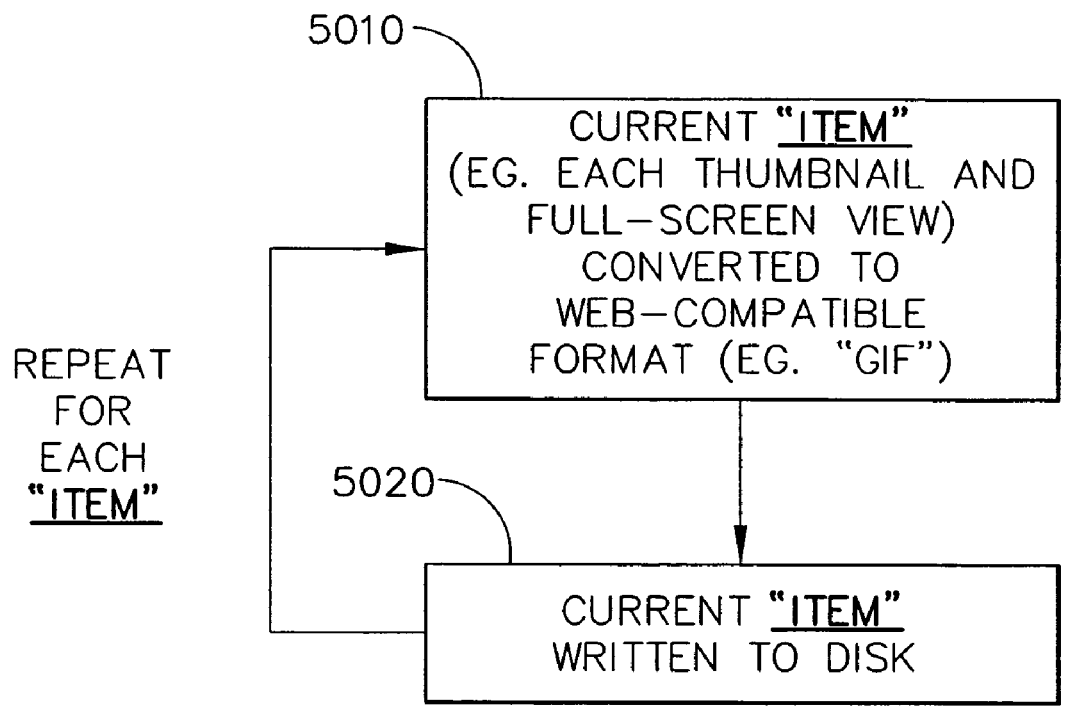
FIG. 8 depicts steps for converting the image to a browser compatible format.

The encoding engine 26. (FIG. 8) is responsible for converting the images from the raw pixel format to a new format which can be displayed by browsers 14 (Steps 5010-5020). One such format is the graphics interchange format (GIF), which can be used to display images in gray scale or color with or without animation (movies). The conversion is achieved using published definitions of web-compatible image formats and writing appropriate computer code. The images are then saved to disk and the post engine 28 is called.

Figure 9:
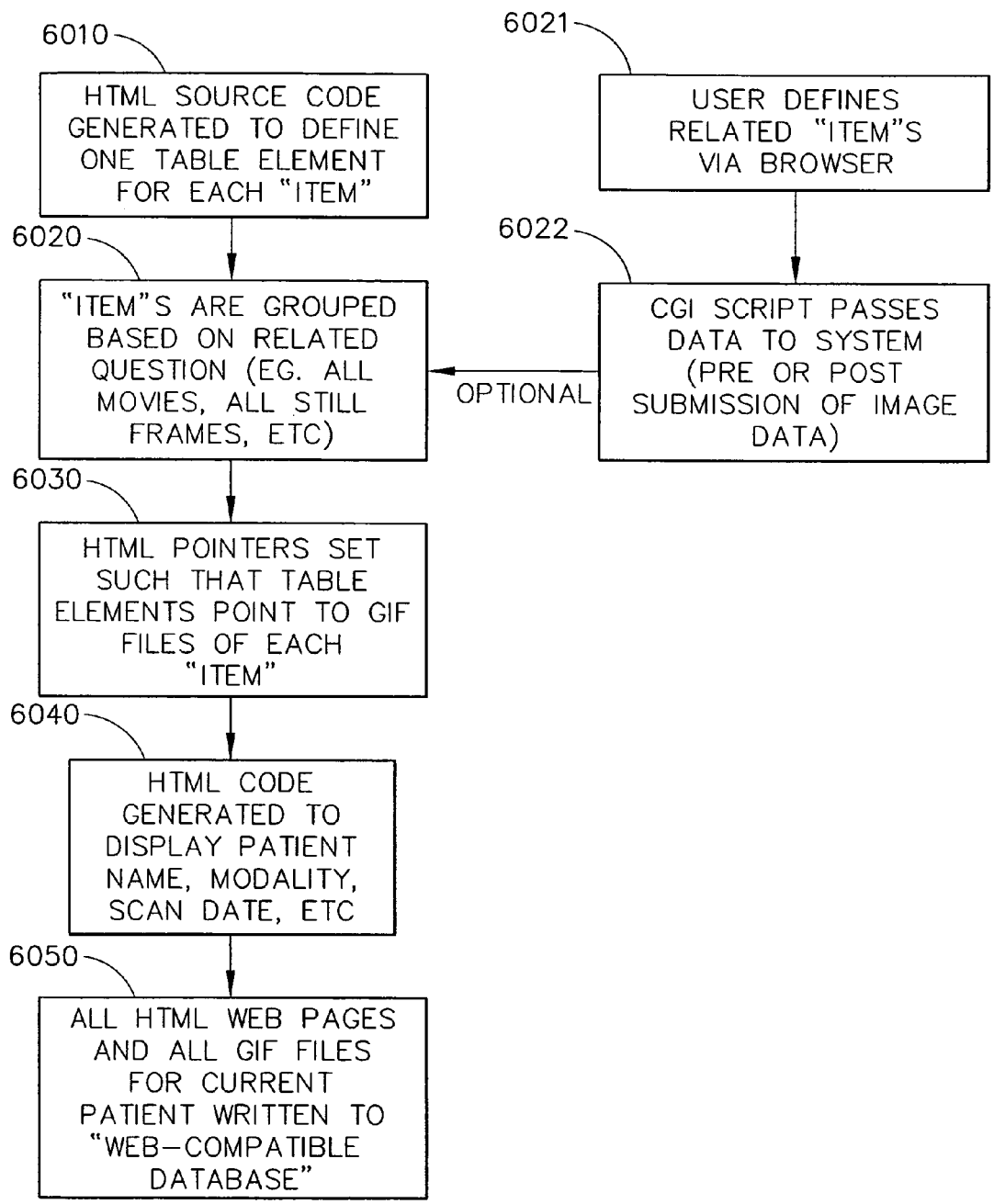
FIG. 9 depicts a method for posting the browser compatible image to a database.

The post engine 28 (FIG. 9) is responsible for generating the html pages within which the images will be displayed (Steps 6010-6030). These html pages may contain coding to display text such as the patient name, exam date, etc. (Step 6040). In addition, the html page will contain html-standard image tags which instruct the browser 14 to display the converted images. The methods by which the html pages are constructed and the image tags embedded are standard to the Internet and are published elsewhere. The final responsibilities (Step 6050) of the post engine 28 are: 1) To transfer the completed html pages and the converted images to the Web-Compatible Database 32 (FIGS. 2 and 3, details FIG. 10) located on the "http Server" 34 for viewing over the Internet; and 2) To send e-mail notification to the physician (or technician) via the e-mail server 30 (FIG. 2) stating that the images have been posted; and 3) providing the http address for the images within the e-mail message such that the physician can "double-click" to immediately view the images.

Once the images are posted as Web Pages, additional Web Pages can be used to allow the technician or physician to rearrange the order of the images on the Web Page according to the diagnostic question. For example, echocardiographic images are often acquired before and after a drug to increase heart rate has been given (e.g., dobutamine). The images before and after the administration of dobutamine are best viewed side-by-side for comparison. Arranging the images side-by-side can be achieved by allowing the user to select images using html standard Web Page "forms." The form data can then be submitted using Web-standard Common Gateway Interface (CGI) protocols and processed by the server using a CGI program written specifically for this purpose. The CGI program could then create a new Web Page in which the image containers are arranged side-by-side and the html "image tags" are set to point to the images defined by the user. Rearrangement of the images occurs very quickly because the images do not require further processing or transfer across the Internet.

Figure 10:
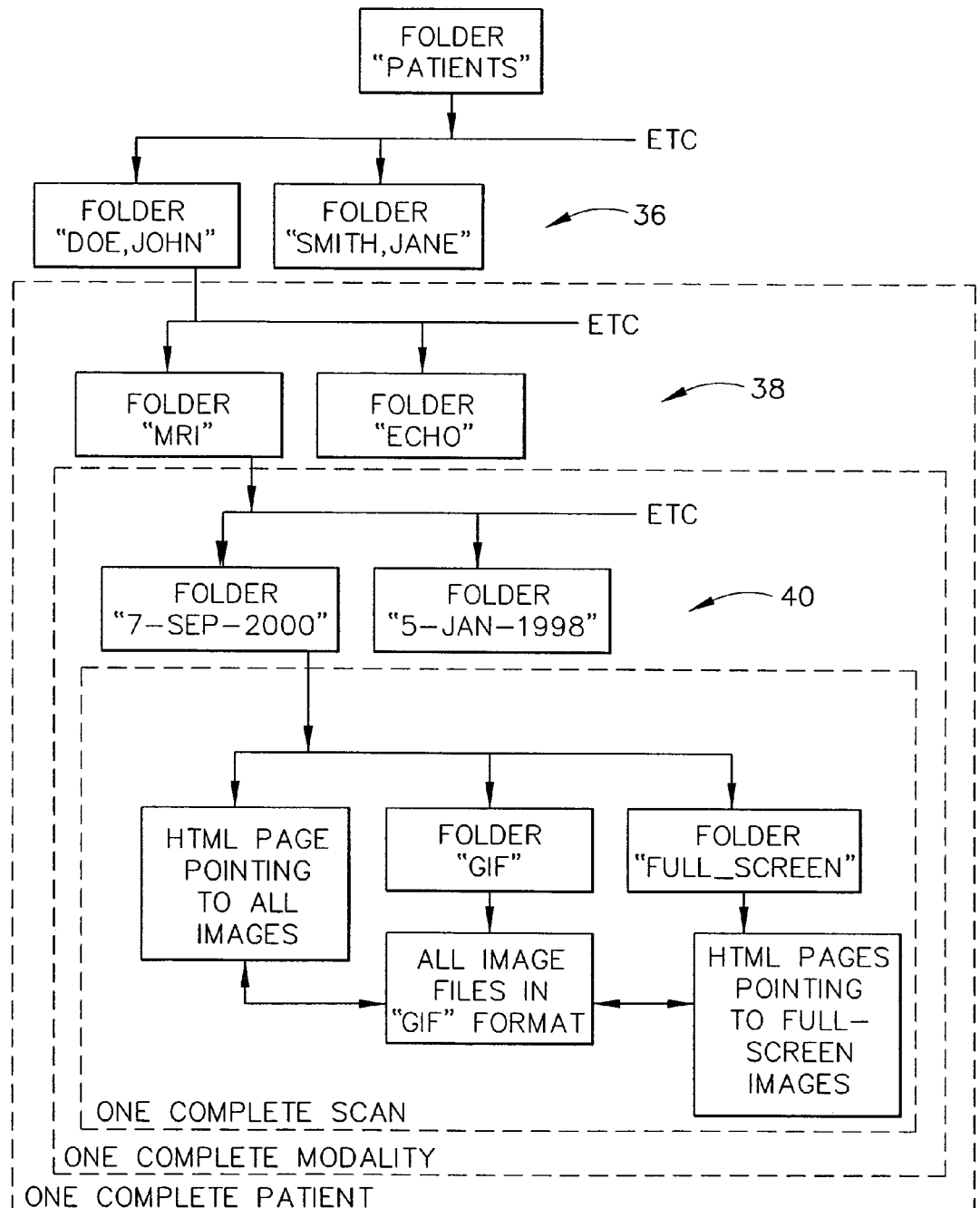
FIG. 10 is a diagram of a file structure for a web compatible database.
Figure 11:
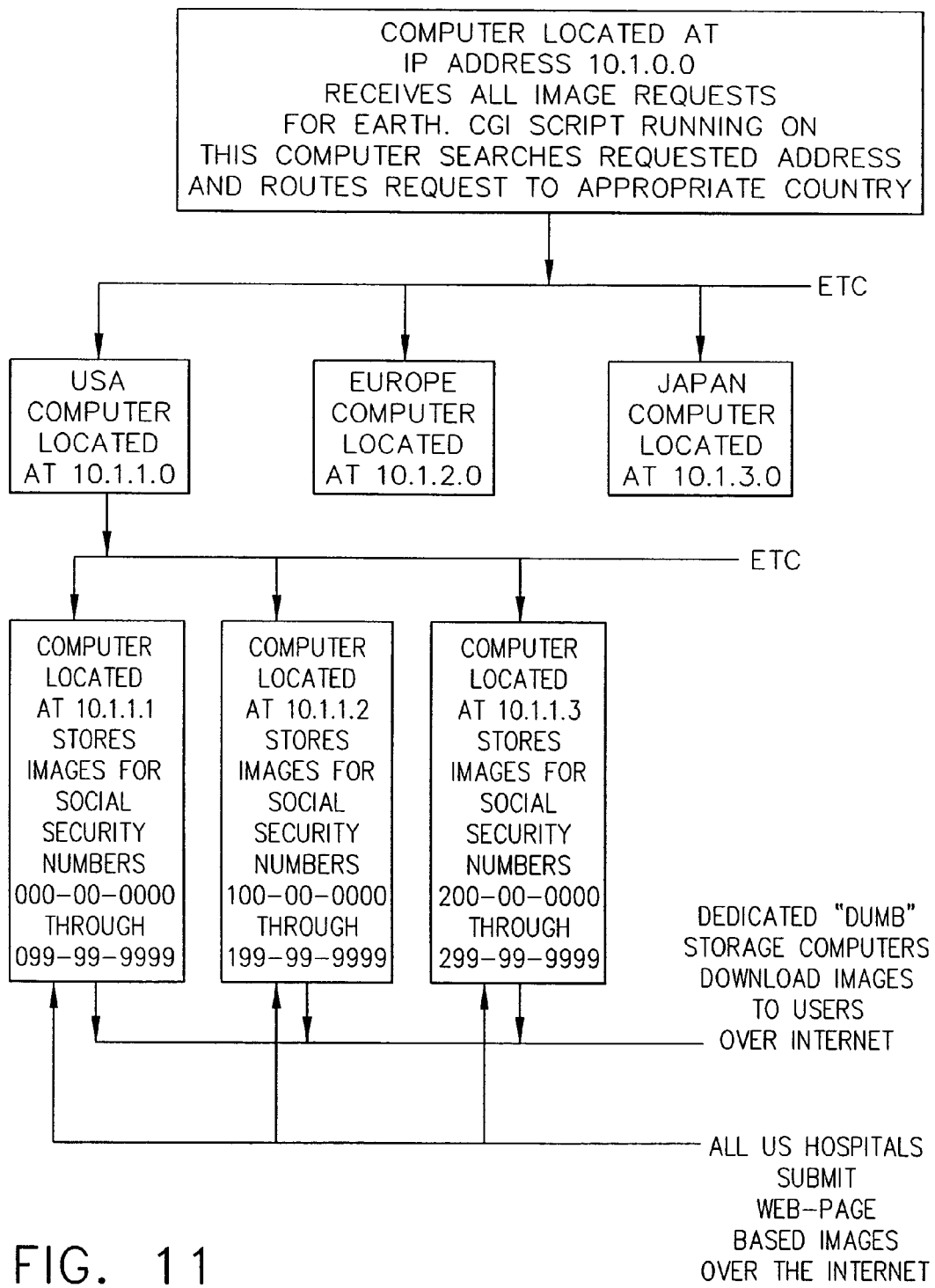
FIG. 11 depicts a possible interface structure for accessing web compatible database via the Internet.

FIG. 11 shows how the Web-Compatible Database 32 of FIG. 10 can be used as the basic building block of a World-wide database which can be interrogated from any location on earth, for example, using any browser 14. In practice, some form of security such as password protection would be provided to prevent unauthorized viewing of the image data.

As shown in FIG. 10, the database 32 is constructed as a hierarchical directory-tree with the patient's name 36 at a higher level than the modality 38. Within each modality subdirectory, a series of directories with names corresponding to the scan date 40 would appear to allow for serial examinations over the patient's lifetime.

Using this type of structure, one can now define a hierarchical Internet addressing system in which any image from any modality for any person acquired on any date will have an unique, pre-determined Internet address. For example, the hierarchical address could involve, first, the Social Security Number of the patient, then the imaging modality, followed by the scan date (See FIG. 12, Step 7010, for example). With this scheme, if a child were born in the U.S. on 11 Jul. 2015, assigned a social security number of 123456789, and later scanned by MRI on 23 Sep. 2027, everyone in the world would know, a priori, that those images will be located at, for example, Internet address:

http://www.imagedatabase.com/usa/123456789/mri/23sep2027. Further, it is, also a priori, known that any MRI images of that patient taken anywhere, anytime in his/her lifetime are listed by scan date at: http://www.imagedatabase.com/usa/123456789/mri, and further that all images of any modality that have ever been acquired of that patient in his/her lifetime are listed at: http://www.imagedatabase.com/usa/123456789.

The section of the URL "www.imagedatabase.com" refers to the company offering to serve the images over the Internet. Such a company would not process the images in any way because the images have already been processed as described herein. Rather, the sole function of such a company is to provide computing hardware which reads the "static" image data from a hard disk and pushes the data over the Internet (note that both still-frame images and movies are contained in "static" computer files). Because the images are already stored in the format of Internet Web Pages, no processing of the data is required resulting in maximum speeds for image access and transfer and ensuring minimum cost for the overall system.

In fact, specialized computers which are capable of no function other than reading from a hard disk and pushing the data over the Internet already exist and could easily be assembled into a array of servers providing access to an extremely large amount of data over the Internet for minimum cost. For example, currently a commercial system of this type provides 120 GB of storage for $3000. With 10 MB of image data per patient scan (typical), this system would provide permanent Internet access to 12,000 complete MRI patient scans for a cost of 25 cents each (exclusive of electrical and maintenance costs). Importantly, this type of World-wide database would be difficult if not impossible to construct if the processes described herein were not employed.

Figure 12:
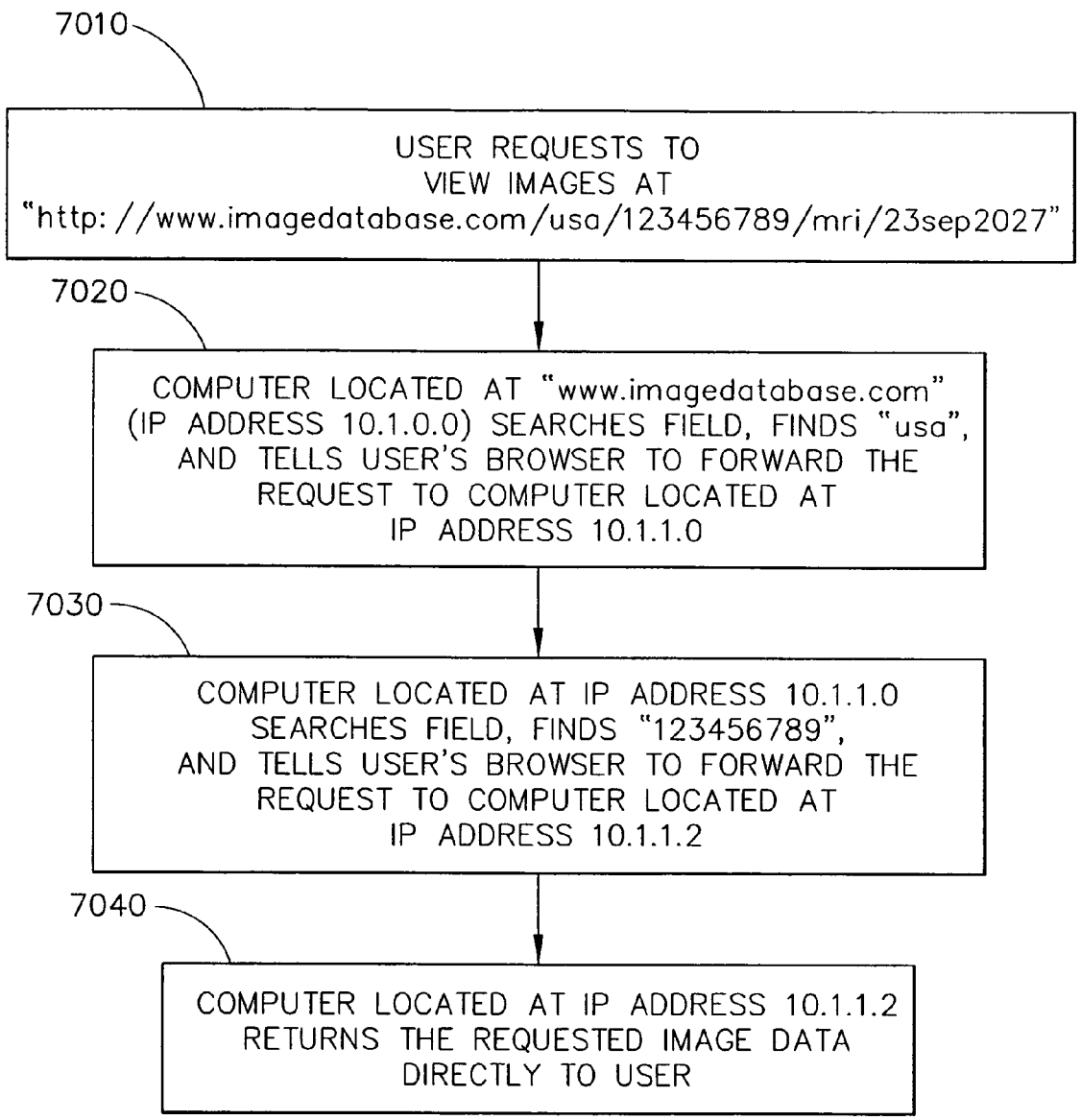
FIG. 12 depicts a method for displaying an image stored on a web compatible database accessible via the Internet.
Figure 13:
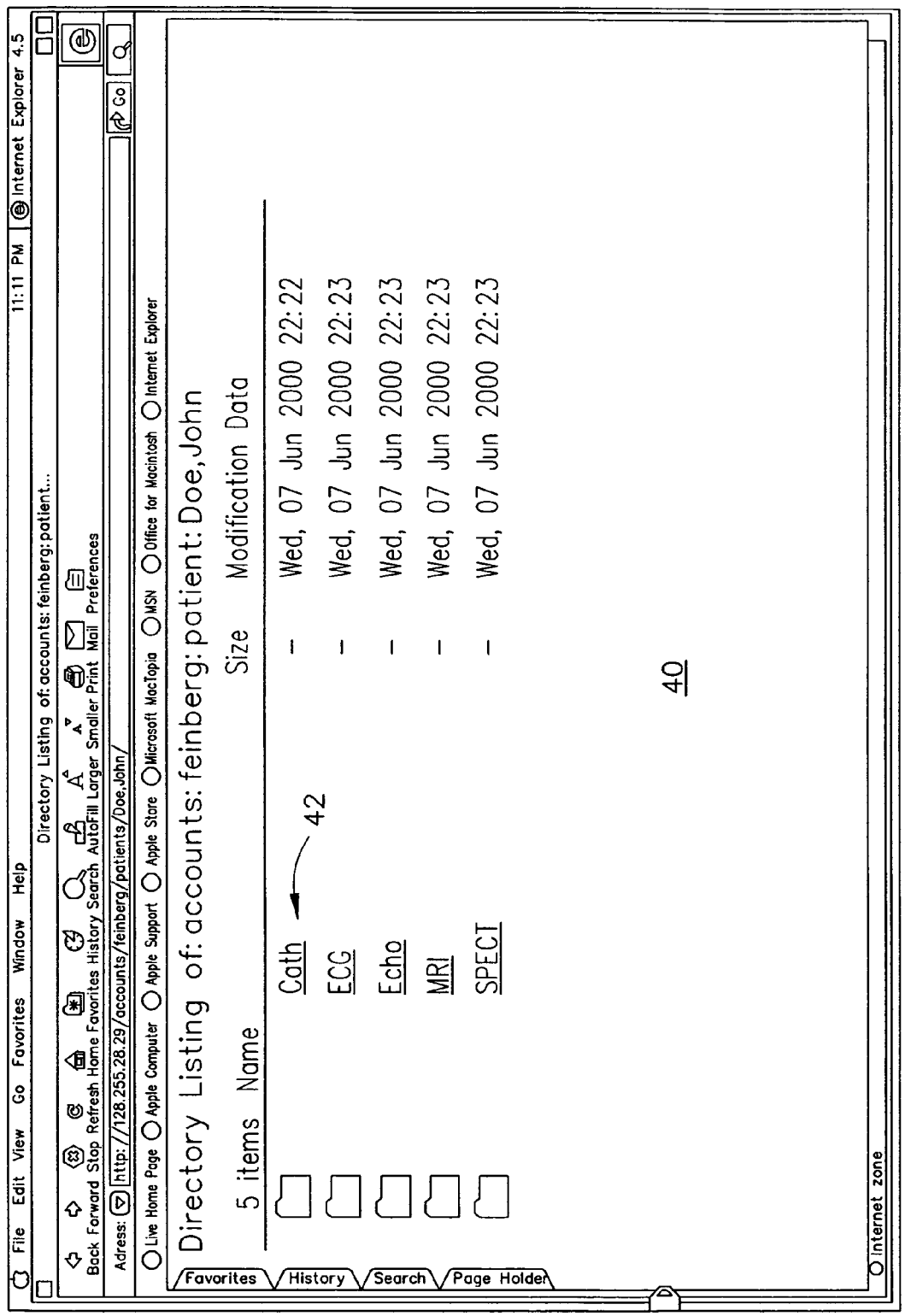
FIG. 13 depicts a selection of modalities for a patient, namely Doe, John.
Figure 14:
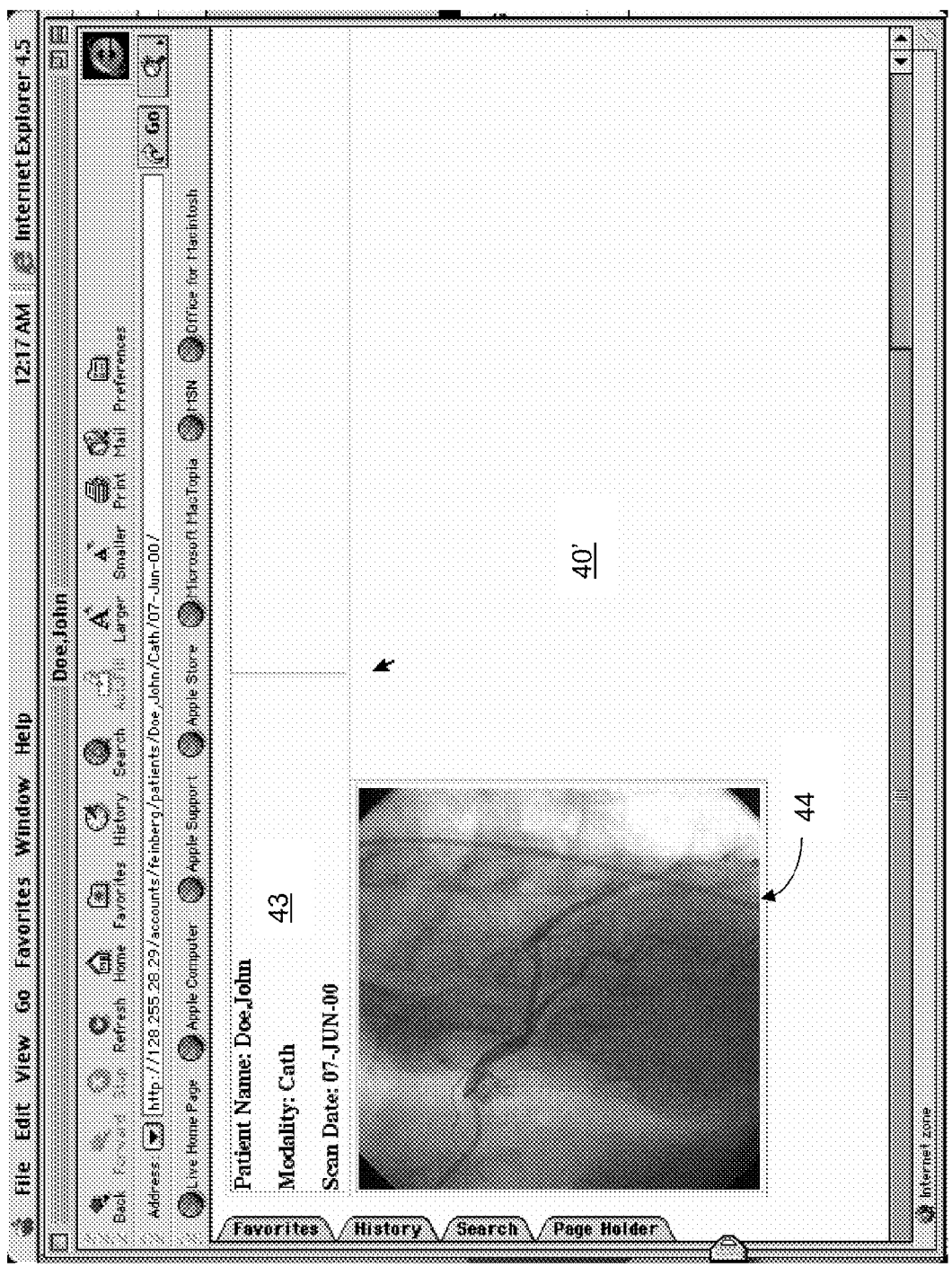
FIG. 14 shows a image identification data obtained from a separate file displayed with the medical image.
Figure 15:
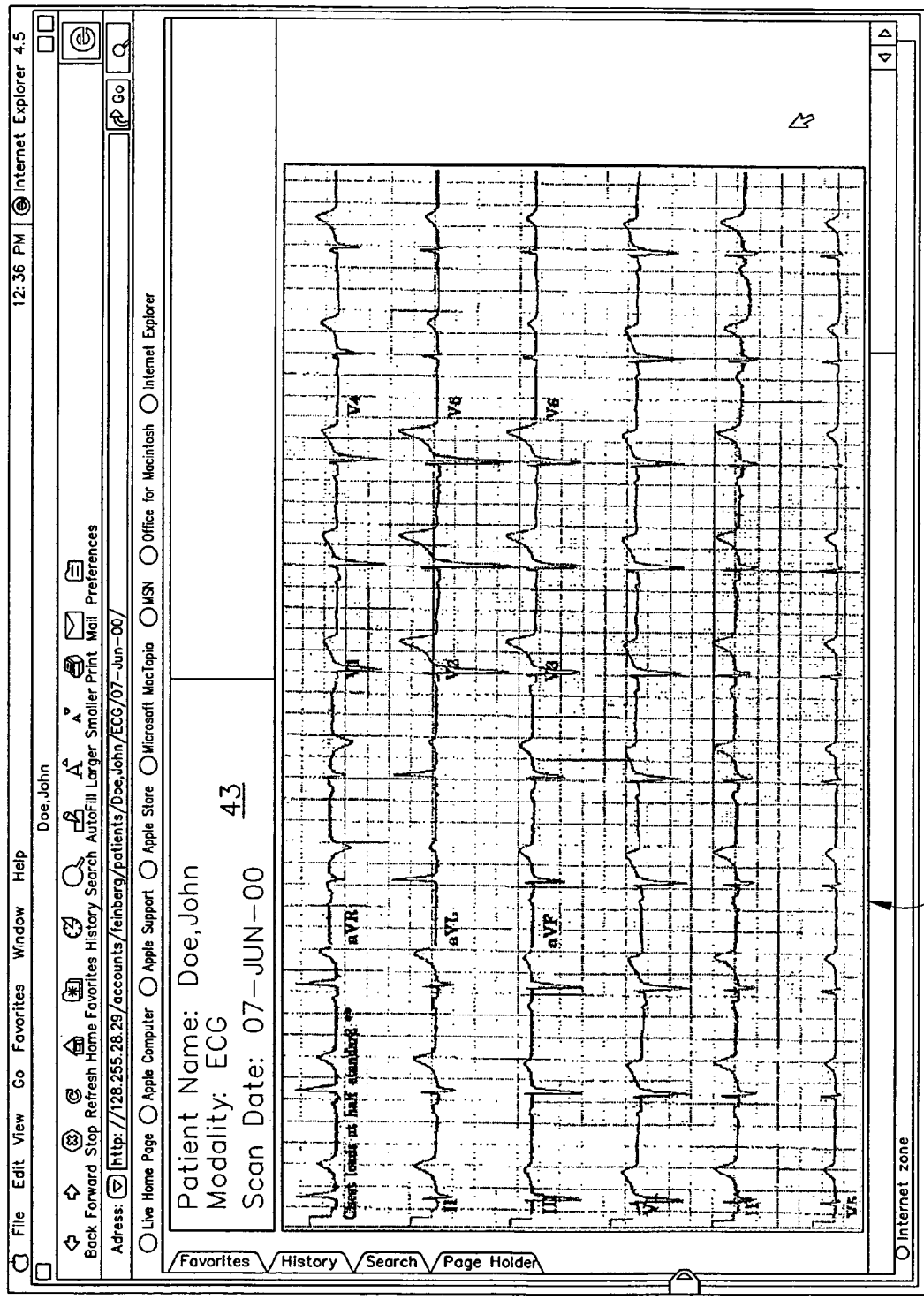
FIG. 15 depicts a web page comprising ECG medical image data.
Figure 16:
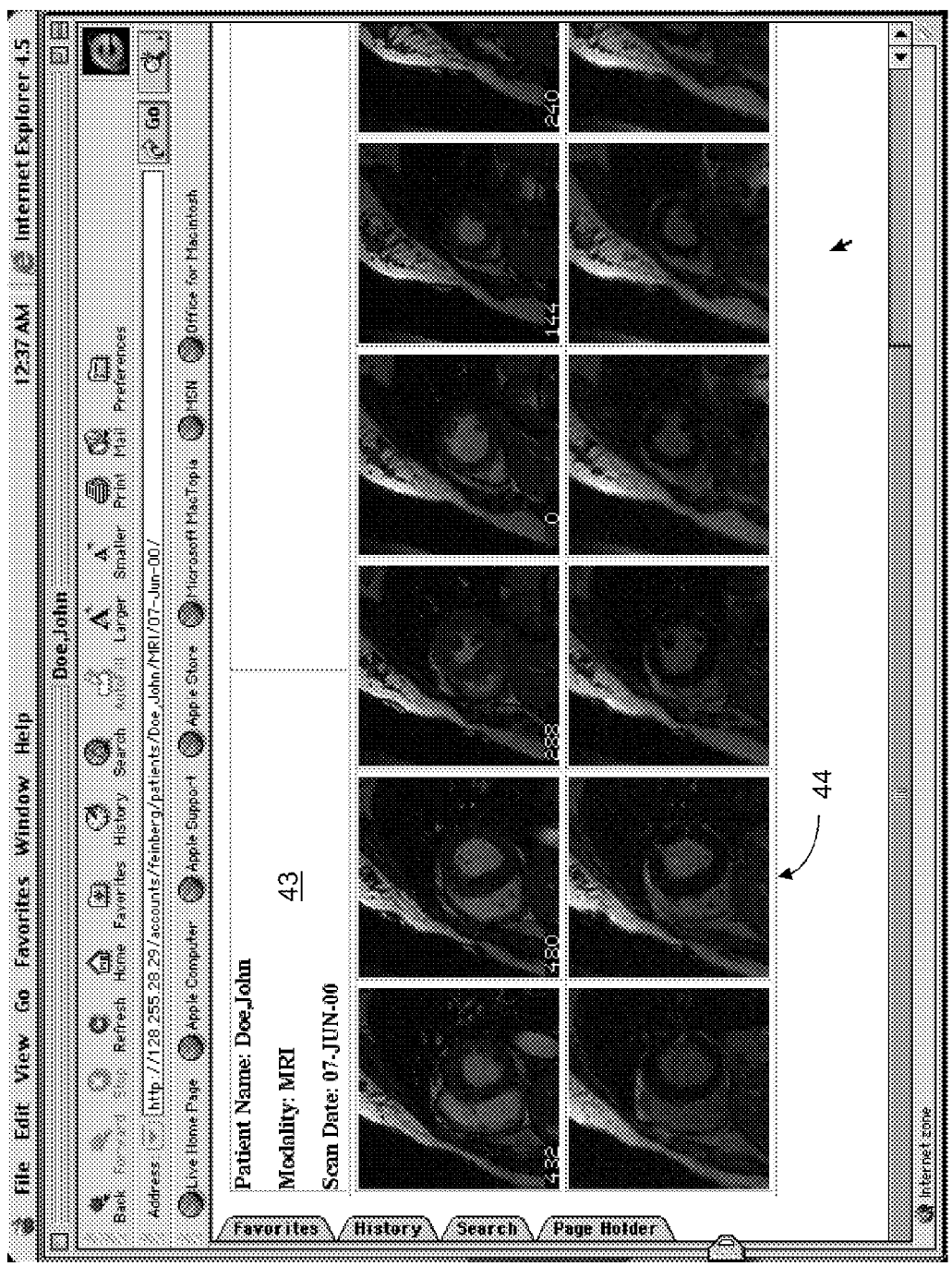
FIG. 16 depicts MRI medical image.
Figure 17:
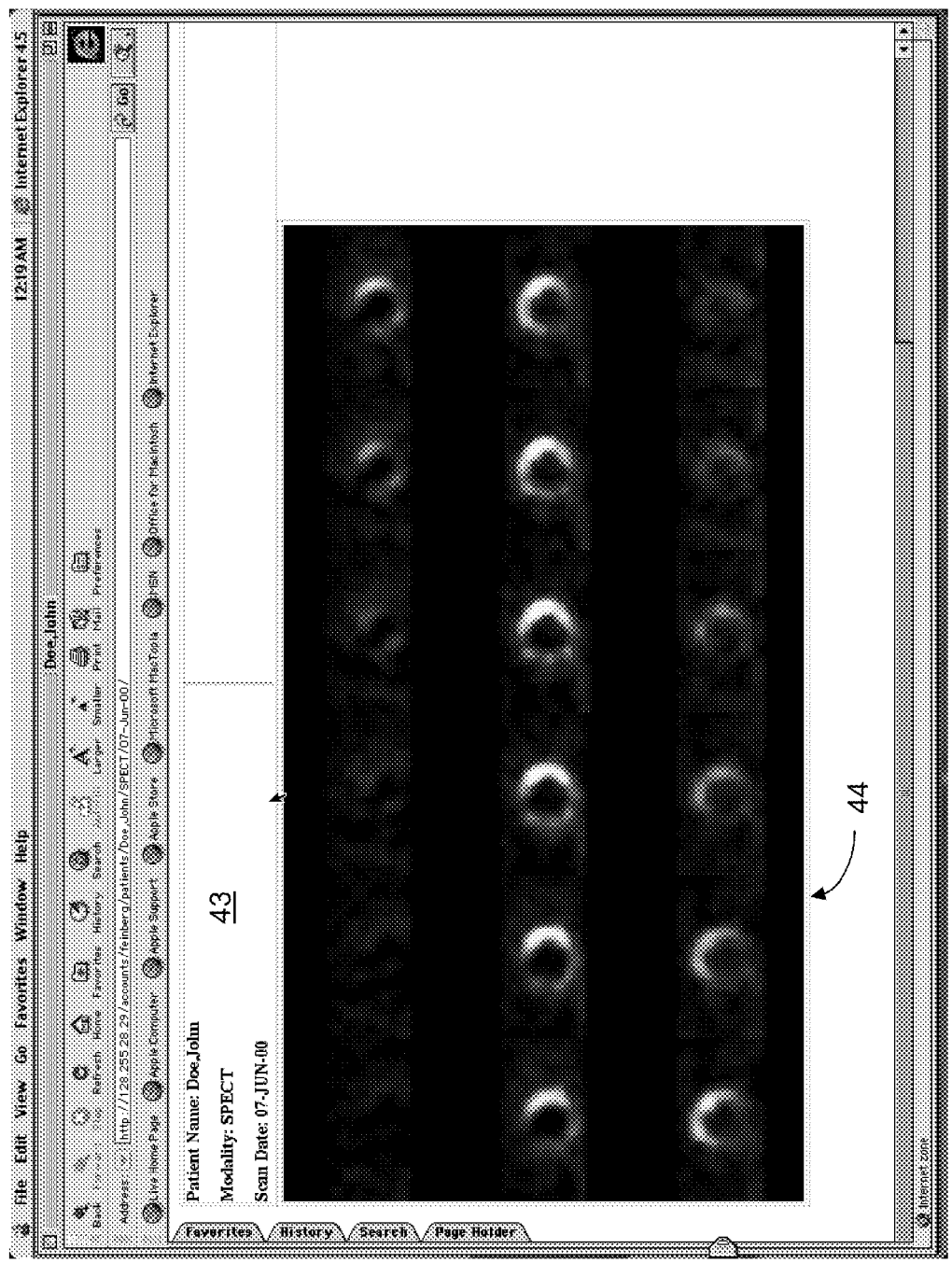
FIG. 17 depicts SPECT medical image data.

FIG. 12 shows how a user's request to view images (Step 7010) would be processed (Steps 7020-7040) by the World-wide database system of FIG. 11 using the basic building block of FIG. 10. FIG. 13 shows the resultant Web Page 40 displaying in response to a user sending a request to view "/Doe, John" via a browser 14. FIG. 14 shows the result of clicking on "Cath" 42 (see FIG. 13) followed by clicking on the scan date (not shown). Identification data 43 is displayed with the image 44 corresponding to the examination data indicated. The html page 40' and the embedded images 44 are sent by the http server 34 to the browser 14. The images 44 can be still frames or movies depending on how they were originally acquired by the scanner 16. In the case of movies, animated GIF format can be used by the encoding engine 26. FIGS. 15, 16 and 17 show the result of clicking on ECG, MRI, and SPECT, respectively. The time necessary to transfer the images 44 from the http Server 34 to the browser 14 will depend on the size of the images 44 and the speed of the network, but was measured to be approximately 3 seconds for the entire set of MRI images of FIG. 16 over a standard ethernet 10BASET line (note that the top row of MRI images in FIG. 16 are movies displaying heart contraction).

The processes described herein can be used as the basis for a worldwide electronic medical record system which simultaneously provides access for both clinical and research purposes at minimal cost.

Figure 18:
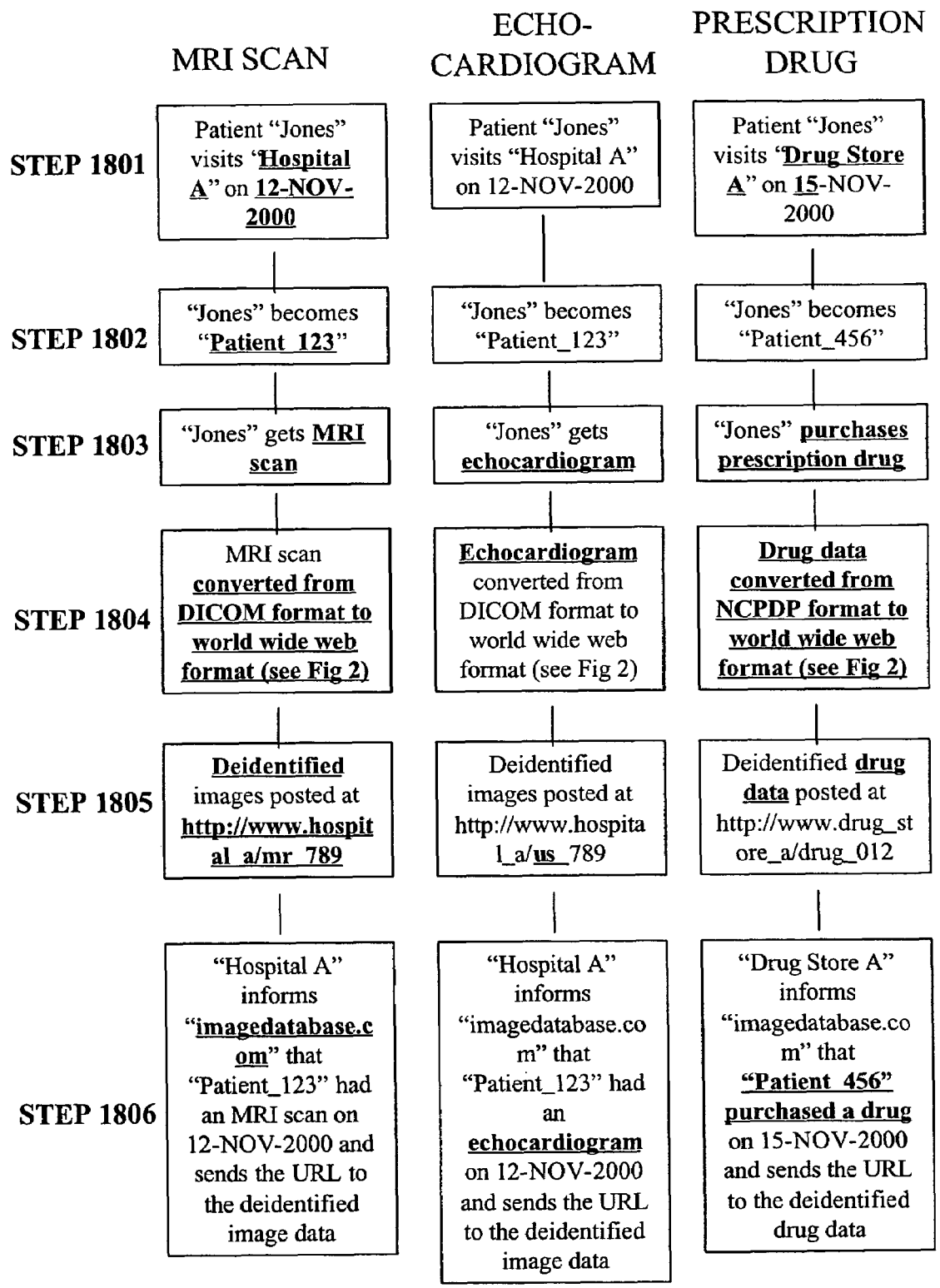
FIG. 18 depicts the processing of three exemplary medical records from the same patient generated by two different medical providers.

As an example, FIG. 18 illustrates patient "Jones" who is admitted to "Hospital A" (Step 1801) and is assigned a unique identifier of "Patient_123" (Step 1802). Patient "Jones" then receives both an MRI and an echocardiogram on "12-NOV-2000" (Step 1803). Images from both examinations are converted (Step 1804) from a format incompatible with the World Wide Web, such as, for example, DICOM Version 3.0, to World Wide Web format using the processes depicted in FIG. 2.

Prior to posting the images on the World Wide Web, however, two additional steps are taken. First, the Web server is configured such that the images are provided over the World Wide Web without displaying the patient's name and other legally protected identifiers (Step 1805). Optionally, the date of the procedure can also be obscured to further protect the patient's privacy. Second, "Hospital A" sends an electronic message to the organization depicted in FIG. 12, "imagedatabase.com", stating that "Patient_123" had an MRI and an echocardiogram on "12-NOV-2000" and: that the medical information can be viewed at http://www.hospital_a.edu/mr_789 and http://www.hospital_a.edu/us_789, respectively (Step 1806). Optionally, during this Step, the unique identifier "Patent_123" could be encrypted to form a different unique identifier in order to hide the internal unique identifier that "Hospital A" uses to identify patient "Jones" without losing the ability to associate multiple records within the same patient).

Three days later, patient "Jones" visits "Drug Store A" (Step 1801) which assigns him a unique identifier of "Patient_456" (Step 1802) allowing "Jones" to purchase a prescription drug (Step 1803). In order to be reimbursed by a health insurance company, as required by Federal Law, "Drug Store A" then embeds the National Drug Code (NDC) and the drug dosage into an electronic message whose format is incompatible with the World Wide Web, namely Telecommunication Standard Version 5.1 of the National Council for Prescription Drug Programs (NCPDP). Additionally, however, "Drug Store A" uses the processes shown in FIG. 2 to convert the NCPDP message into a format compatible with the World Wide Web (Step 1804). The patient's name and other legally protected identifiers are removed (Step 1805) from the drug code and dose which appear on the World Wide Web. "Drug Store A" then sends an electronic message to "imagedatabase.com" (Step 1806) stating that "Patent_456" purchased a drug on "15-NOV-2000" and that the NDC and dose can be viewed at http://www.drug_store_a/drug_012. Again, a different unique identifier could be introduced at this step without losing the ability to associate multiple records from the same patient.

Two weeks later, patient "Jones" exercises his legal right to access his medical information from "Hospital A" and learns that his unique identifier is "Patient 123" (or its optionally encrypted value). Similarly, he learns from "Drug Store A" that his unique identifier is "Patent_456". In an effort to collect all of his medical information in one place, patient "Jones" informs "imagedatabase.com" that "Patent_123" at "Hospital A" and "Patent_456" at "Drug Store A" are both him (Step 1807, FIG. 19).

Figure 20:
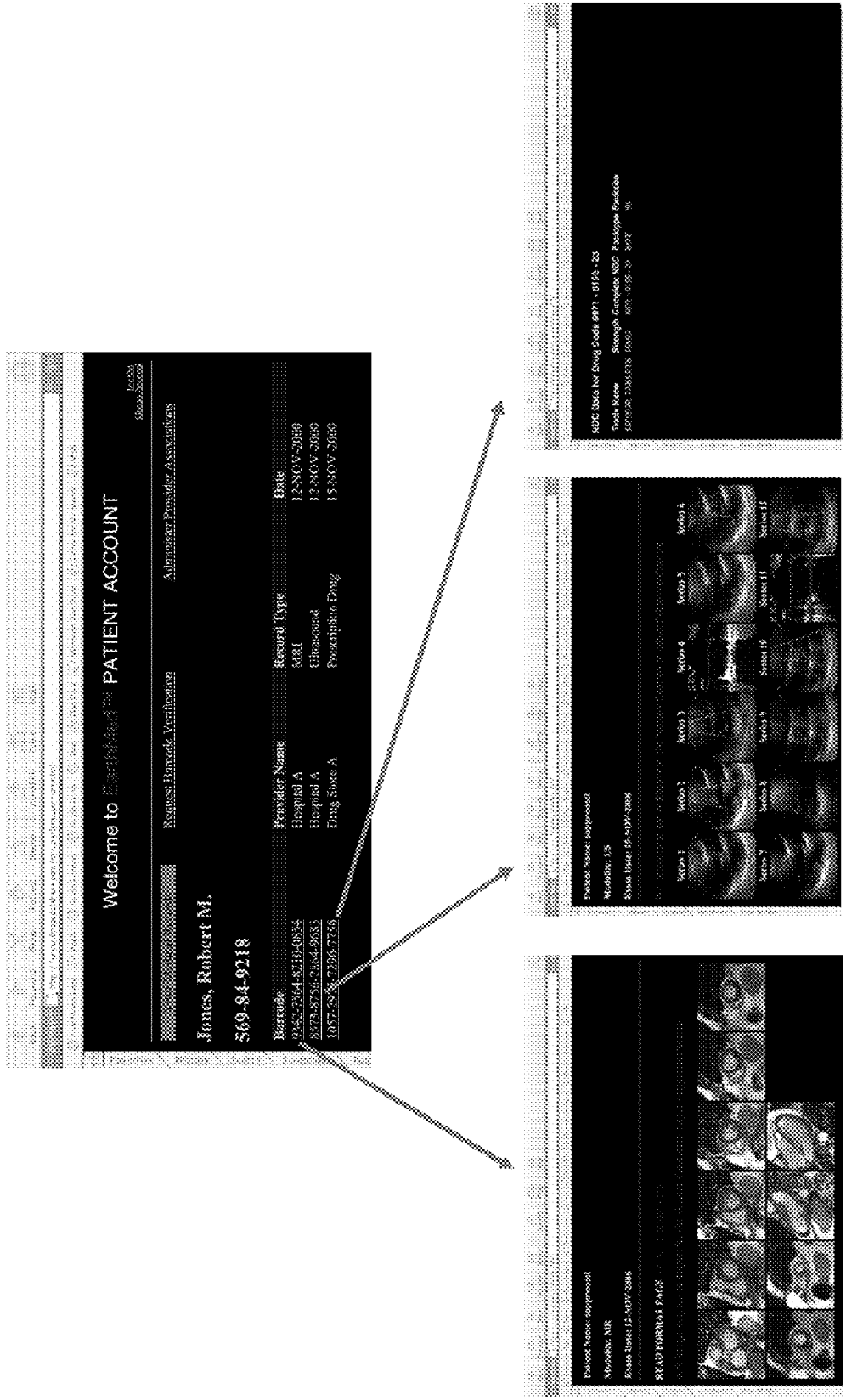
FIG. 20 depicts clinical access to the medical information of FIG. 18.

One month later, patient "Jones" visits a different physician in a different geographic location and can quickly access all of his medical information by visiting www.imagedatabse.com (FIG. 20). Images from both the MRI and the echocardiogram can be viewed by clicking on World Wide Web links, provided by imagedatabase.com, which point to http://www.hospital_a.edu/mr_789 and http://www.hospital_a.edu/us_789, respectively. Similarly, the drug code and dose purchased by "Jones" can be viewed at http://www.drug_store_a/drug_012 (FIG. 20). Access of this type represents the "Clinical (Private) View" of the information stored by "imagedatabase.com" and is made possible by the organizational structure of the database table shown in FIG. 19. Optionally, the database table of FIG. 19 could contain a second URL which accesses the same medical information but allows the patient's name to appear on the web page during "Private" access.

Importantly, neither the images nor the drug data need to be stored by "imagedatabase.com". Rather, the links at www.imagedatabase.com can point to the raw medical information physically stored by "Hospital A" and "Drug Store A" yet accessible via the World Wide Web. Using this approach, the additional costs which society would incur by storing the same medical information at "Hospital A", "Drug Store A", and "imagedatabase.com" can be avoided; there is only one physical copy of each official medical record.

Figure 21:
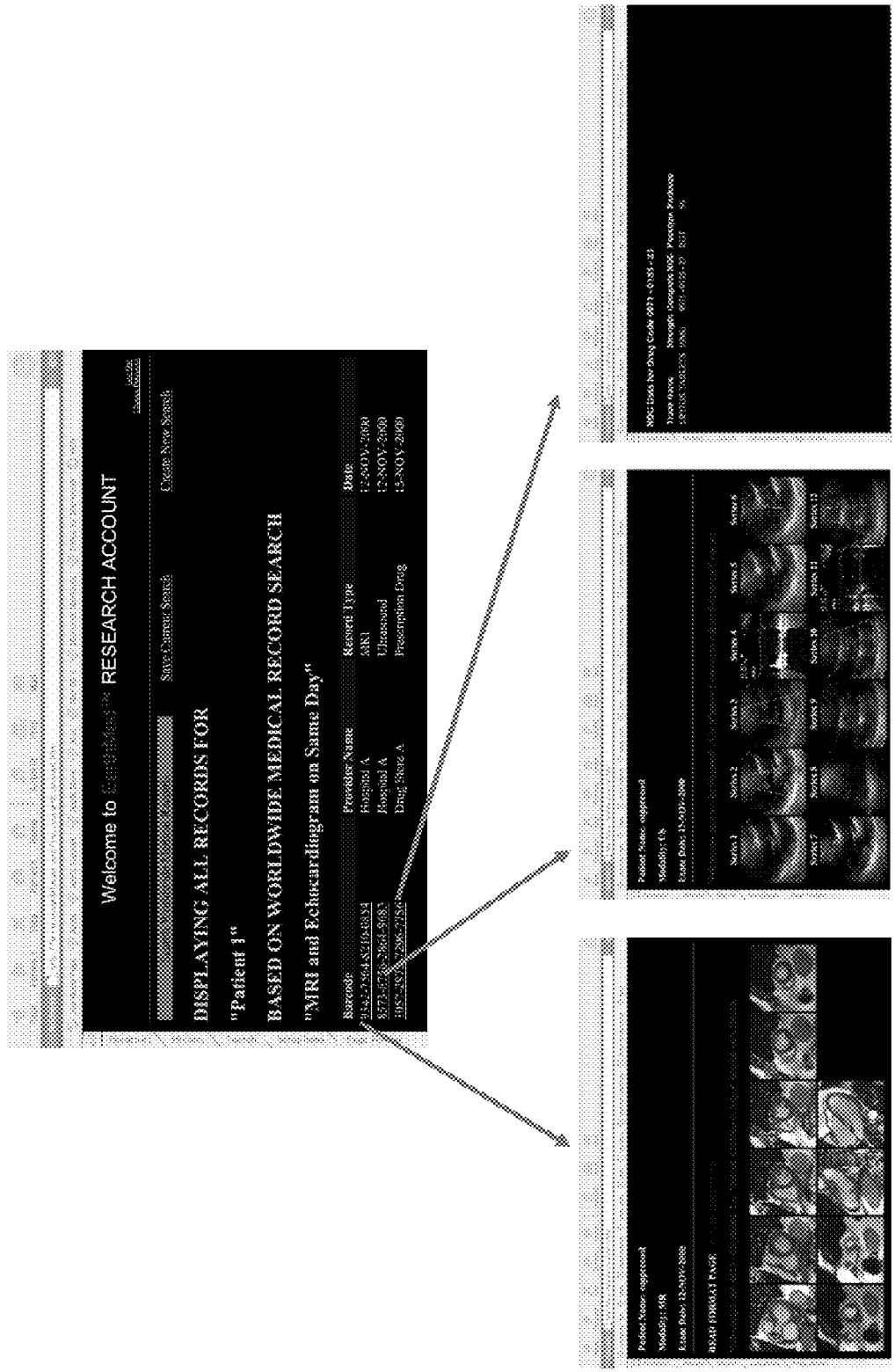
FIG. 21 depicts research access to the medical information of FIG. 18.

In addition to this clinical utility, however, research can now be performed on the same medical information without additional cost. As shown in FIG. 21, a researcher physically located anywhere in the world can query the information system located at www.imagedatabase.com to learn if any patient received both an MRI scan and an echocardiogram on the same day. The system located at www.imagedatabase.com will respond "yes, and the same patient purchased a prescription drug three days later". The researcher can view both sets of images as well as the drug code and dose (FIG. 21). Despite access to all of this patient's medical records, however, it is impossible for the researcher to discover that the name of the patient is "Jones". Access of this type represents the "Research (Public) View" of the information stored by "imagedatabase.com" and is again made possible by the organizational structure of the database table shown in FIG. 19. Importantly, while the raw medical information (images, drug data, etc.) can be used for two distinct purposes, clinical care and research, the overall system design minimizes costs to society because worldwide there is still only one physical copy of the raw medical information.

Further efficiencies can be realized by modifying individual steps in the overall process. For example, FIG. 22 shows two methods by which data enters the database table physically located at "imagedatabase.com". In Method A, individual health care providers employ differing clinical reporting systems physically located at the provider's institution. These physically distributed reporting systems are programmed to send electronic messages to "imagedatabase.com". In Method B, conversely, a single, centralized reporting system is physically located at "imagedatase.com" and clinical reports are generated by remotely-located physicians by use of a Web Server. Method B, therefore, decreases costs because the multiple disparate reporting systems are replaced with a single system with many users, and further facilitates the integration of information across multiple sites while maintaining web based access.

The processes described herein, therefore, provide the basis for a worldwide electronic medical record system in which geographically distributed records, all of which are associated within individual patients, can be accessed by anyone from anywhere. The identity of an individual patient can only be determined if the patient exercises the legal right to learn which records belong to them. The cost of such a system is minimized by the fact that medical information is stored only once, at its point of origin, and by the fact that the underlying system design is based on the World Wide Web.

Thus, using the Present Invention a database of images ban be constructed with maximum Internet performance and without loss of diagnostic information. Importantly, the processes described herein allow viewing of images from multiple modalities side-by-side by the primary physician and/or the patient. Further, the database structure facilitates the storage of image data from multiple modalities and multiple scans over a patient's lifetime in a single location identified by the patient's name, social security number or other unique identifier. This ability would be expected to significantly enhance the ability of the primary physician to determine the course of action which is in the best interest of the patient.

While the Present Invention has been particularly shown and described with reference to particular embodiments thereof, it will be understood by those skilled in the art that various changes in form and detail may be made therein without departing from the spirit and scope of the Present Invention. The scope of the Present Invention, as claimed, is intended to be defined by following Claims as they would be understood by one of ordinary skill in the art with appropriate reference to the specification, including the drawings, as warranted.

What is claimed is:

1. A method of managing medical information comprising:
   de-identifying medical information of a patient, comprising replacing an identity of the patient with a unique identifier;
   converting the de-identified medical information into a format compatible with viewing in an Internet web browser;
   posting the de-identified medical information on a web server for access from the Internet web browser;
   informing a web database of the posting of the de-identified medical information to form a web database record pointing to the posted and de-identified medical information, wherein informing a web database comprises sending to the web database an electronic message comprising an Internet address of the posted and de-identified medical information; and
   associating a plurality of de-identified medical information of the patient, comprising querying a plurality of web database records for the unique identifier.

2. The method of claim 1, wherein the message further comprises at least one of a modality type of the de-identified medical information, the unique identifier, and a date that the medical information is first acquired of the patient.

3. The method of claim 1, further comprising encrypting the unique identifier to form an encrypted identifier.

4. The method of claim 1, further comprising associating a plurality of de-identified medical information of the patient residing on a plurality of servers, comprising querying the plurality of web database records for a plurality of unique identifiers corresponding to the patient.

5. The method of claim 4, wherein a plurality of health care providers post the plurality of de-identified medical information on the plurality of web servers, wherein each of the plurality of health care providers assigns a different one of the plurality of unique identifiers to the patient than the other of the plurality of health care providers.

6. The method of claim 4, further comprising providing user access from the Internet web browser to the associated plurality of de-identified medical information of the patient corresponding to the plurality of unique identifiers, wherein the plurality of de-identified medical information is accessible to the user in one of a de-identified format where an identity of the patient is inaccessible or an identified format where the identity of the patient is accessible.

7. A method of managing medical information comprising:
   encrypting a unique identifier associated with de-identified medical information of a patient;
   converting the de-identified medical information into a format compatible with viewing in an Internet web browser;
   posting the de-identified medical information on a web server for access from the Internet web browser;
   informing a web database of the posting of the de-identified medical information to form a web database record pointing to the posted and de-identified medical information, wherein informing a web database comprises sending to the web database an electronic message comprising an internet address of the posted and de-identified medical information; and
   associating a plurality of de-identified medical information of the patient, comprising querying a plurality of web database records for the encrypted identifier.

8. The method of claim 7, wherein encrypting a unique identifier comprises replacing the unique identifier with an encrypted identifier.

9. The method of claim 7, wherein a plurality of encrypted identifiers correspond to the patient.

10. The method of claim 9, wherein the plurality of de-identified medical information of the patient is posted on a plurality of web servers.

11. The method of claim 10, further comprising associating the plurality of de-identified medical information of the patient, comprising querying the plurality of web database records for the plurality of encrypted identifiers corresponding to the patient.

12. The method of claim 11, further comprising providing user access from the Internet web browser to the associated plurality of de-identified medical information of the patient corresponding to the plurality of encrypted identifiers, wherein the plurality of de-identified medical information is accessible to the user in one of a de-identified format where an identity of the patient is inaccessible or an identified format where the identity of the patient is accessible.

* * * * *